United States Patent
Zakay et al.

(10) Patent No.: US 10,610,350 B2
(45) Date of Patent: Apr. 7, 2020

(54) SPRING-POWERED, HYDRAULICALLY-OPERATED INTRAOCULAR LENS INSERTER

(71) Applicant: Atrion Corporation, Allen, TX (US)

(72) Inventors: Avraham Zakay, Tel Aviv (IL); Raz Ben Yaakov, D.N. Hof Carmel (IL); Jonathan D Collins, Arab, AL (US); Daniel M Swantner, Owens Cross Roads, AL (US); Gregory A Yarbrough, Arab, AL (US)

(73) Assignee: Halkey-Roberts Corporation, St. Petersburg, FL (US)

( * ) Notice: Subject to any disclaimer, the term of this patent is extended or adjusted under 35 U.S.C. 154(b) by 0 days.

(21) Appl. No.: 15/133,015

(22) Filed: Apr. 19, 2016

(65) Prior Publication Data

US 2018/0333253 A1    Nov. 22, 2018

Related U.S. Application Data

(60) Provisional application No. 62/219,700, filed on Sep. 17, 2015, provisional application No. 62/149,650, filed on Apr. 19, 2015.

(51) Int. Cl.
*A61F 2/16*    (2006.01)
(52) U.S. Cl.
CPC .................... *A61F 2/167* (2013.01)
(58) Field of Classification Search
CPC .......... A61F 2/1662–1678; A61F 2/167; A61F 2/148; A61F 9/0008
See application file for complete search history.

(56) References Cited

U.S. PATENT DOCUMENTS

| 5,232,687 | A | * | 8/1993 | Geimer | A61F 9/0008 424/400 |
| 5,613,957 | A | * | 3/1997 | Py | A61F 9/0008 222/321.9 |
| 5,702,441 | A | | 12/1997 | Zhou | |
| 5,881,956 | A | * | 3/1999 | Cohen | A61F 9/0008 239/333 |
| 9,155,656 | B2 | * | 10/2015 | Schaller | A61F 9/00781 |
| 9,402,716 | B2 | * | 8/2016 | Novak | A61F 2/167 |

(Continued)

FOREIGN PATENT DOCUMENTS

EP    0937443 B1    8/1999

*Primary Examiner* — Katrina M Stransky
*Assistant Examiner* — Brigid K Byrd
(74) *Attorney, Agent, or Firm* — GrayRobinson, P.A.

(57) ABSTRACT

An intraocular lens inserter for use during cataract surgery for delivering an intraocular lens (IOL) loaded into an IOL cartridge into a patient's eye. The inserter comprises an outer shell housing containing a hydraulic housing. A hydraulic piston positioned within the hydraulic housing defines an annular hydraulic chamber. The hydraulic chamber is filled with a fluid via a fill port. A high pressure compression spring constantly urges the piston forwardly to pressurize the fluid in the hydraulic chamber. During use, a valve element operatively connected to a depressible operation button, controls bleeding of fluid from the hydraulic chamber, whereupon the forward tip of the piston is moved forwardly to mechanically deliver the intraocular lens from the IOL cartridge into the patient's eye.

31 Claims, 29 Drawing Sheets

(56) References Cited

U.S. PATENT DOCUMENTS

| | | | |
|---|---|---|---|
| 2001/0007075 A1* | 7/2001 | Hjertman | A61F 2/1667 606/107 |
| 2002/0074362 A1* | 6/2002 | Py | A61F 9/0008 222/388 |
| 2002/0082609 A1* | 6/2002 | Green | A61F 2/1662 606/107 |
| 2005/0023300 A1* | 2/2005 | Schultz | A61F 9/0008 222/383.1 |
| 2005/0065534 A1* | 3/2005 | Hohl | A61F 2/1678 606/107 |
| 2006/0235430 A1* | 10/2006 | Le | A61F 2/148 606/107 |
| 2007/0027538 A1* | 2/2007 | Aharoni | A61F 2/1613 623/6.12 |
| 2007/0208422 A1* | 9/2007 | Walter | A61F 2/142 623/5.11 |
| 2007/0270945 A1* | 11/2007 | Kobayashi | A61F 2/1664 623/6.12 |
| 2008/0004596 A1* | 1/2008 | Yun | A61M 25/0084 604/508 |
| 2008/0027460 A1* | 1/2008 | Kobayashi | A61F 2/1662 606/107 |
| 2008/0183145 A1* | 7/2008 | Peclat | A61M 11/06 604/298 |
| 2008/0255579 A1* | 10/2008 | Wollenhaupt | A61F 2/1675 606/107 |
| 2009/0018548 A1* | 1/2009 | Charles | A61F 2/1662 606/107 |
| 2009/0292293 A1* | 11/2009 | Bogaert | A61F 2/1664 606/107 |
| 2010/0082037 A1* | 4/2010 | Kobayashi | A61F 2/1675 606/107 |
| 2010/0160926 A1 | 6/2010 | Artsyuckhovich et al. | |
| 2011/0301538 A1 | 12/2011 | Stammen | |
| 2012/0289970 A1 | 11/2012 | Pynson | |
| 2013/0190703 A1* | 7/2013 | Greiner-Perth | B05B 11/0067 604/295 |
| 2013/0245544 A1* | 9/2013 | de Juan, Jr. | A61F 9/0017 604/44 |
| 2014/0012277 A1* | 1/2014 | Matthews | A61F 2/1675 606/107 |
| 2014/0257317 A1 | 9/2014 | Safabash | |
| 2014/0276898 A1* | 9/2014 | Novak | A61F 2/167 606/107 |
| 2014/0276901 A1* | 9/2014 | Auld | A61F 2/1678 606/107 |
| 2015/0088149 A1* | 3/2015 | Auld | A61F 2/1678 606/107 |
| 2015/0209178 A1* | 7/2015 | Blakey | B05B 11/309 604/290 |
| 2015/0282928 A1* | 10/2015 | Auld | A61F 9/007 623/6.12 |
| 2015/0342726 A1* | 12/2015 | Deacon | A61F 2/148 623/6.12 |
| 2016/0015511 A1* | 1/2016 | Auld | A61F 2/167 606/107 |
| 2017/0071787 A1* | 3/2017 | Canelli | A61F 9/00736 |
| 2018/0168800 A1* | 6/2018 | Kaegi | A61F 2/1672 |
| 2018/0333253 A1* | 11/2018 | Zakay | A61F 2/167 |

* cited by examiner

LOADING THE UNFOLDER PLATINUM 1 SERIES CARTRIDGE

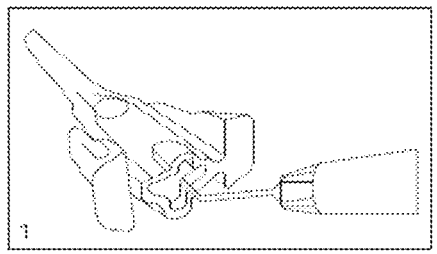

APPLY OVD

Remove cartridge from the inner tray and fill completely with HEALON viscoelastic

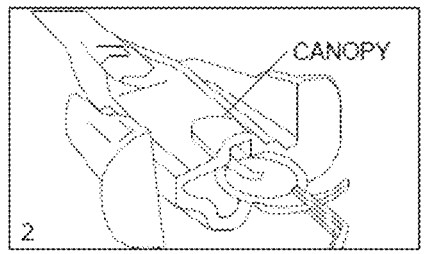

FOLD LEADING HAPTIC OVER OPTIC

Grasp the lens with forceps by the optic edge only and hold the cartridge with the IOL diagram facing up. Engage the lead haptic with the canopy and sweep the lead haptic over the optic body in one motion half the optic inside the cartridge. Ensure that the lead haptic is fully tucked over the optic body.

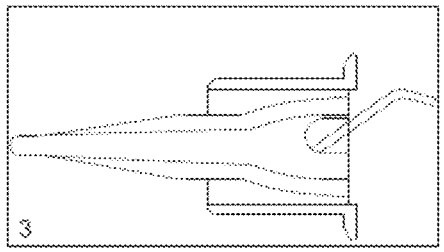

TUCK TRAILING HAPTIC WITH FORCEPS

Grasp the trailing haptic with forceps and tuck it over the optic body.

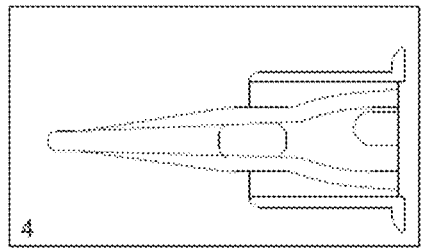

ADVANCE IOL IN CARTRIDGE

Using forceps, advance the lens past the marked on the cartridge. Ensure that the lens and haptics remain folded in place after removing forceps.

FIG. 9A

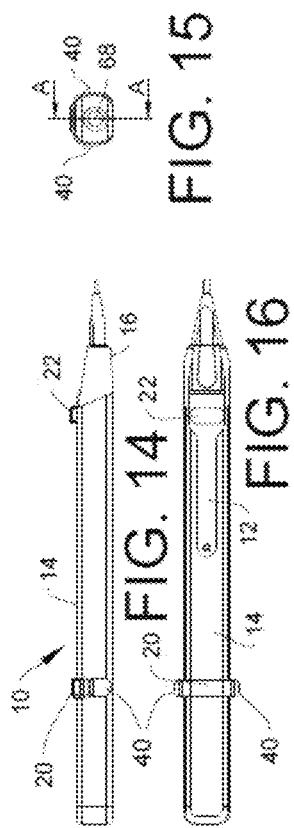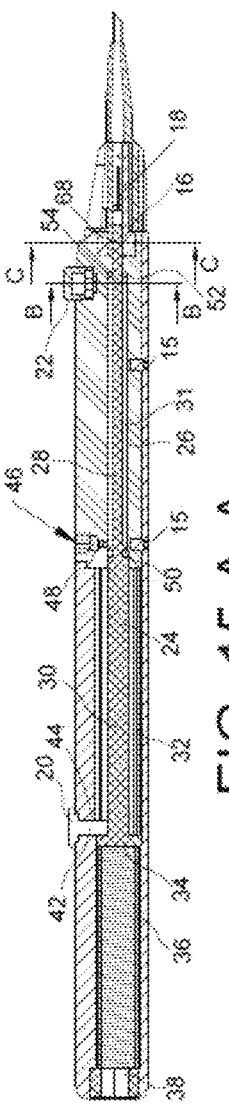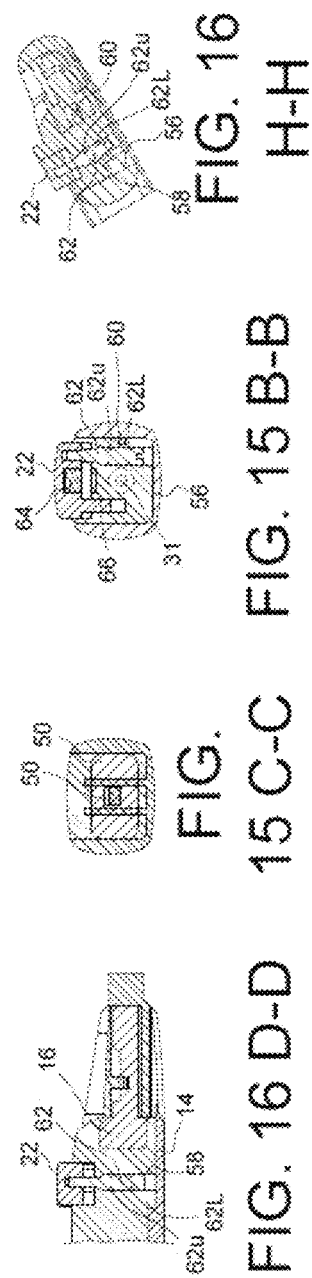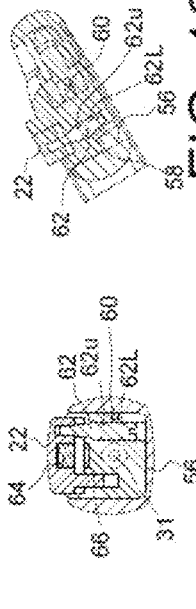

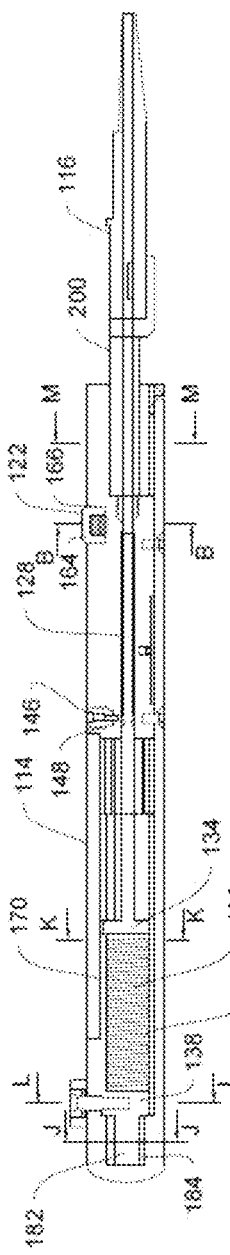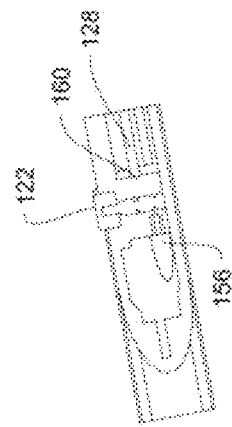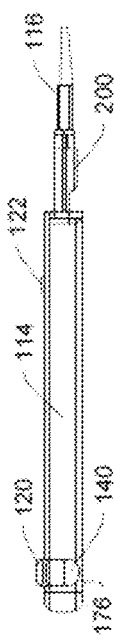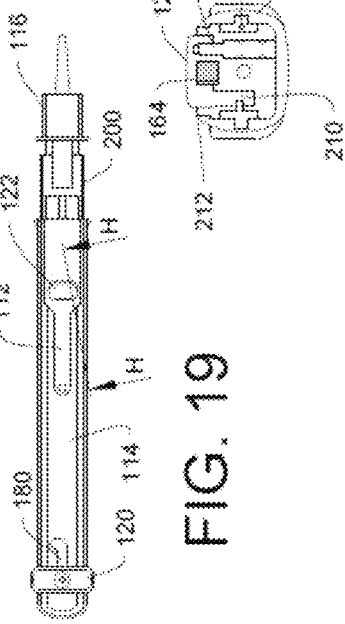
FIG. 17
FIG. 18 A-A
FIG. 18
FIG. 19
FIG. 18 B-B
FIG. 19 H-H

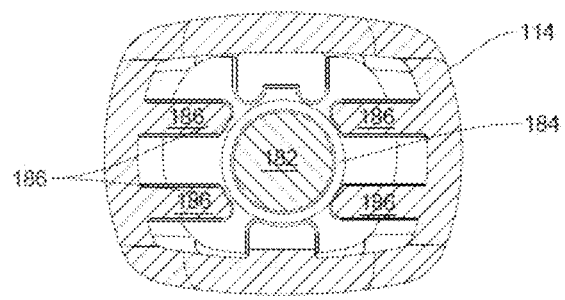
FIG. 18 J-J
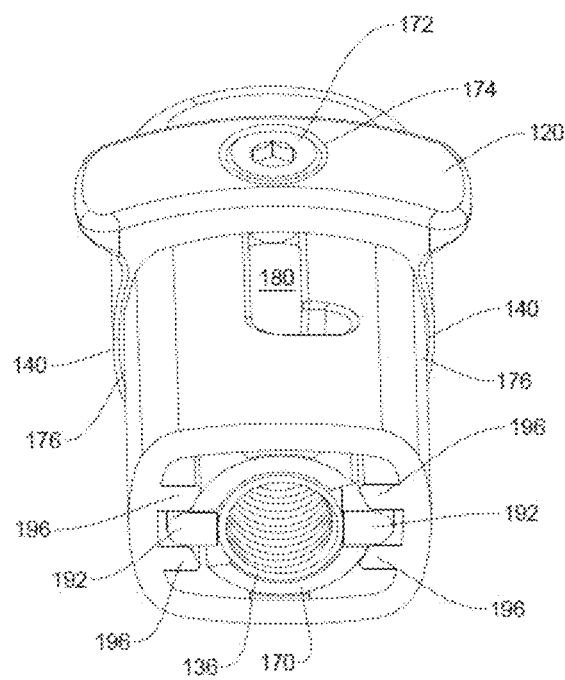
FIG. 18 K-K

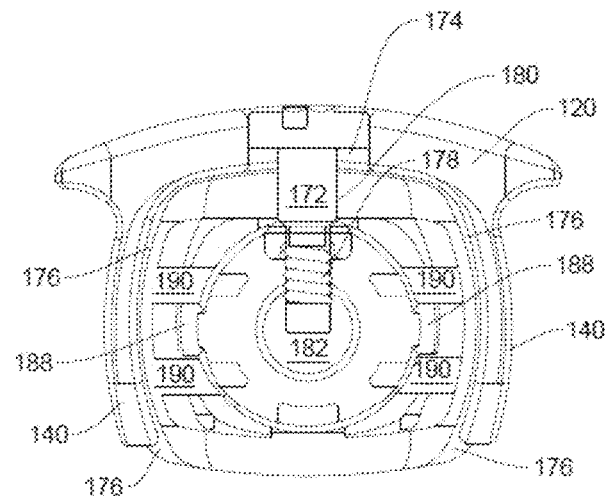
FIG. 18 L-L
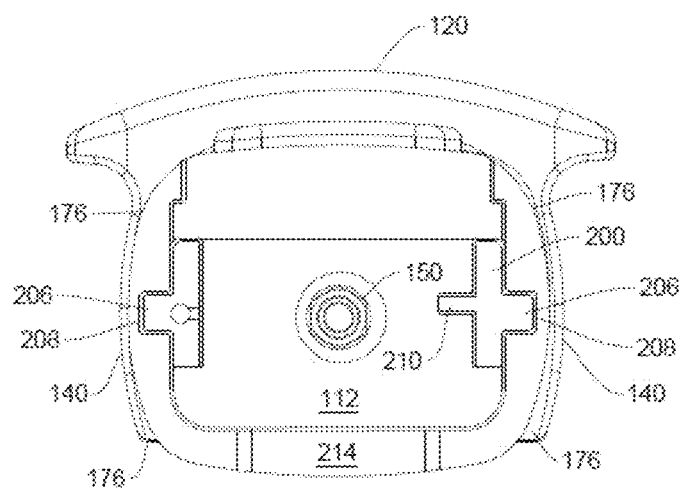
FIG. 18 M-M

SPRING-POWERED, HYDRAULICALLY-OPERATED INTRAOCULAR LENS INSERTER

CROSS REFERENCE TO RELATED APPLICATIONS

This application claims the benefit of provisional application Ser. No. 62/219,700, filed Sep. 17, 2015 and of provisional application Ser. No. 62/149,650, filed Apr. 19, 2015, the disclosures of which are each hereby incorporated by reference herein.

BACKGROUND OF THE INVENTION

Field of the Invention

This invention relates to intraocular lens inserters for inserting an intraocular lens (IOL) through a small clear corneal incision of an eye into the capsular opening (capsulorhexis) and to its final position within the capsular bag.

Description of the Background Art

Representative prior art IOL inserters include Published United States Patent Application 2014/0276901 and European Patent EP 0 937 443 B1, the disclosures of both of which are hereby incorporated by reference herein.

It is an object of this invention to provide an improvement which provides an improvement which is a significant contribution to the advancement of the IOL inserter art.

Another object of this invention is to provide a one-handed, spring-powered IOL inserter that operates hydraulically by a finger-operated operation valve to smoothly deliver the IOL continuously at a constant speed into the patient's eye while minimizing irregular movement that might otherwise result in the IOL being inserted too erratically into the eye or overshooting the IOL into the eye.

Another object to this invention is to provide an IOL inserter that is adaptable to use commercially available IOL folding and delivery chambers manufactured by IOL manufacturers.

Another object of this invention is to provide a spring-powered, hydraulically-operated IOL inserter that dispenses an initial amount of ophthalmic viscoelastic fluid into the IOL folding and delivery chamber to wet the chamber and smoothly fold of the IOL into position for delivery.

Another object of this invention is to provide a spring-powered, hydraulically-operated IOL inserter composed of biocompatible materials that is sufficiently economical to manufacture to be capable of being a single-use (i.e., disposable) IOL inserter.

The foregoing has outlined some of the pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

For the purpose of summarizing this invention, this invention comprises a spring-loaded piston that pushes an ophthalmic viscoelastic (OVD) fluid to achieve both restrained, constant IOL speed and lubrication, a single OVD filling port using about 0.5 ml OVD (per industry standard), and a third-party pre-loaded IOL delivery system having a lens folding and delivery chamber. In a first embodiment, the lens folding and delivery cartridge comprises the AcrySert C preloaded injector manufactured by Alcon, Inc. to insert Alcon's AcryS IQ IOL. In second and third embodiments, the lens folding and delivery cartridge comprises the Unfolder Platinum Series Cartridge manufactured by Abbott Medical Optics Inc. to insert Abbott's Tecnis 1-Piece Aspheric IOL. However, it shall be appreciated that other third-party delivery systems (e.g., Hoya Surgical Optics' iSert® 231/251 Preloaded IOL systems) may be alternatively employed without departing from the spirit and scope of this invention.

As shown in FIG. 1, the first embodiment of the IOL inserter of the invention comprises, a generally elongated outer shell including a spring chamber, an OVD filling port, a piston window, an operation button, a safety pin, and the AcrySert delivery system having a lens window and a tip for inserting into a 2.2 mm incision.

The interior of the IOL inserter of the first embodiment of the invention is shown in FIG. 2 and comprises a spring, piston, hydraulic mechanism housing, operation button and AcrySert delivery system.

As shown in FIG. 3, the piston includes O-rings at both ends to prevent fluid leakage. In one embodiment of the invention, the properties of the spring may include those reflected in FIG. 3.

As shown in FIG. 4, the hydraulic mechanism comprises an OVD filling port check valve, allowing filling of an OVD chamber with OVD from a syringe filled with OVD, which flows from the OVD chamber through an opening into the valve cavity (see Section A).

As shown in FIG. 5, after filling of the OVD chamber via the syringe, OVD fluid flows through a conduit into the AcrySert lens chamber to fill the same.

The injector operation is summarized as follows. As shown in FIG. 6, in Step 1 the OVD chamber is filled with OVD via the OVD filling port check valve. During this step, the safety pin holds the valve open allowing the OVD fluid to flow via the conduit into the AcrySert delivery system. The syringe containing the supply of OVD fluid delivers sufficient fluid to fill the OVD chamber and the AcrySert delivery system via the conduit up to the indicated fill line in the tip of the system. The safety pin also locks the piston.

Referring to FIG. 7, Step 2 of the injector operation includes removing the safety pin whereupon the valve is released and moves upward by means of its spring to its closed position to close the conduit. Removal of the safety pin also releases the piston.

In Step 3 shown in FIG. 8, by depressing the operation button to partially open the valve, the IOL is advanced while folding it by means of the piston to its folded position. It is noted that the button includes stoppers to prevent the valve from moving all the way down. Continued depressing of the operation button then delivers the folded IOL into the eye.

The second embodiment of the IOL Inserter of the invention shown in FIG. 9 comprises a design similar to the first embodiment. However, the second embodiment of the IOL Inserter is adapted to be used in conjunction with the IOL folding and delivery Cartridge known as the "Unfolder Platinum Series Cartridge" manufactured by Abbott Medical Optics Inc. to insert Abbott's Tecnis 1-Piece Aspheric IOL. The second embodiment further improves upon the first embodiment to operate in following manner.

First, as shown in FIG. 9, the surgical assistant loads the IOL into the IOL Cartridge wetted with OVD fluid. The surgical assistant fills the Hydraulic Housing via a Fill Port with OVD fluid. The IOL Cartridge is then inserted into the proximal end of a Slider of the IOL inserter. As shown in FIG. 10, the Slider is pushed inwardly into the proximal end of the Outer Shell Housing of the IOL Inserter and held into position by a catch. The inward movement of the Slider closes the Operation Switch.

The surgical assistant then snaps-off the Safety Clasp as shown in FIG. 11, which allows the Release Pin to move slightly forward in a slot in the Outer Shell Housing. The Release Pin is coupled to a spring-loaded Piston Housing (not shown) which moves forwardly to correspondingly move the Piston slightly forward. This slightly forward movement of the Piston forces the IOL into a folded condition in the IOL Cartridge, ready to be inserted into the patient's eye.

As shown in FIG. 12, the surgical assistant then moves the Release Pin off to the side, which internally functions to release the Piston to be subjected to the full force of a high-pressure spring entrained within the Piston Housing against the head of the Piston. The IOL inserter is now in its cocked position.

During the surgical procedure, as the surgeon pushes the Operation Button downwardly using finger pressure, its valve is opened allowing OVD fluid to bleed out of the Hydraulic Housing and thereby allowing the Piston under the force of the spring, to move progressively forwardly and deliver the IOL from the IOL Cartridge into the patient's eye (see FIG. 13).

The third embodiment is illustrated in FIGS. 29-37. As shown in FIGS. 29-31, in the third embodiment, the IOL inserter includes an OVD fill port that is Luer compatible. A spring-loaded charging plunger is operatively positioned in the rear of the outer shell housing. A hydraulic tube (hypo tube) that encircles a portion of the piston fitted with O-rings to defines a hydraulic chamber. The chamber is fluidly connected to a hydraulic housing containing a valve.

As shown in FIGS. 31-32, the hydraulic chamber is fluidly connected to the fill port so that when an OVD-filled syringe is fitted to the Luer fitting of the fill port and OVD is injected therein, the hydraulic chamber is filled with OVD fluid. Also, excess OVD fluid is allowed to flow through a molded-in OVD conduit through a valve of a spring-loaded operation button being held open by a button latching rod. OVD fluid flowing through the open valve and OVD conduit fills the IOL cartridge, such as an AMO Tecnis iTec Pre-loaded Delivery and System Folder and Delivery Chamber.

As shown in FIG. 32, during use, Step 1 comprises filling the hydraulic chamber with OVD fluid until OVD can be seen in front of the IOL to wet the IOL. During Step 1, the valve is held open by means of the button latching rod (see FIG. 33) so that OVD may flow into the IOL cartridge to fill the same to the desired level.

As shown in FIG. 34, Step 2 comprises pushing the charging plunger fully into the rear of the outer shell housing and locking it in place with an audible "click." At the same time, the button latching rod likewise moves forward to release the button from being held in its open position. Upon being released, the button and hence the valve moves upwardly to a closed position, thereby activating the hydraulic valving system. As the charging plunger is pushed fully into the outer shell housing, the piston is advanced into in the IOL cartridge to push the IOL into the manufacturer's recommended 30 second to 10 minute location. It is noted that in this position, the spring of the charging piston is now constantly urging the piston forwardly; however, the piston remains stationary due to the OVD being captured within the hydraulic chamber. The piston may move forward under the force of the spring only when the captured OVD in the hydraulic chamber is bled therefrom by depressing the operation button to re-open the valve.

As shown in FIG. 35, Step 3 involves the surgeon's finger depressing the operation button to re-open the valve whereupon the IOL is moved forwardly into the manufacturer's recommend 1 minute maximum lens folding position in the IOL cartridge. As shown in FIG. 36, continued depressing of the operation button then further advances the piston until the IOL is deployed into the patient's eye.

Finally, as shown in FIG. 37, the third embodiment of the IOL inserter is intended to be co-developed with Abbott to be used with Abbott's IOL cartridge for its Tecnis 1-Piece Aspheric IOL (see also FIG. 9A). However, without departing from the spirit and scope of this invention, the IOL inserter may be adapted to be used with other IOL cartridges of other IOL manufacturers.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which:

FIG. 9 is a perspective view of the second embodiment of the IOL inserter of the invention and FIG. 9A is an instructions-for-use drawing showing the loading of OVD fluid;

FIG. 14 is a side elevational view of the first embodiment of the IOL inserter of the invention;

FIG. 15 is a front elevational view of the first embodiment of the IOL inserter of the invention;

FIG. 16 is a top elevational view of the first embodiment of the IOL inserter;

FIGS. 15A-A, 15B-B, 15C-C; 16D-D, and 16H-H are cross-sectional views thereof along lines A-A, B-B, C-C, D-D, and H-H.

FIG. 17 is a side elevational view of the first embodiment of the IOL inserter of the invention;

FIG. 18 is a front elevational view of the first embodiment of the IOL inserter of the invention;

FIG. 19 is a top elevational view of the first embodiment of the IOL inserter;

FIGS. 18A-A, 18B-B, 19H-H, 18J-J, 18K-K, 18L-L and 18M-M are cross-sectional views thereof along lines A-A, B-B, H-H, J-J, K-K, L-L and M-M.

Similar reference characters refer to similar parts throughout the several views of the drawings.

DETAILED DESCRIPTION OF THE PREFERRED EMBODIMENTS

First Embodiment

Figure 1:
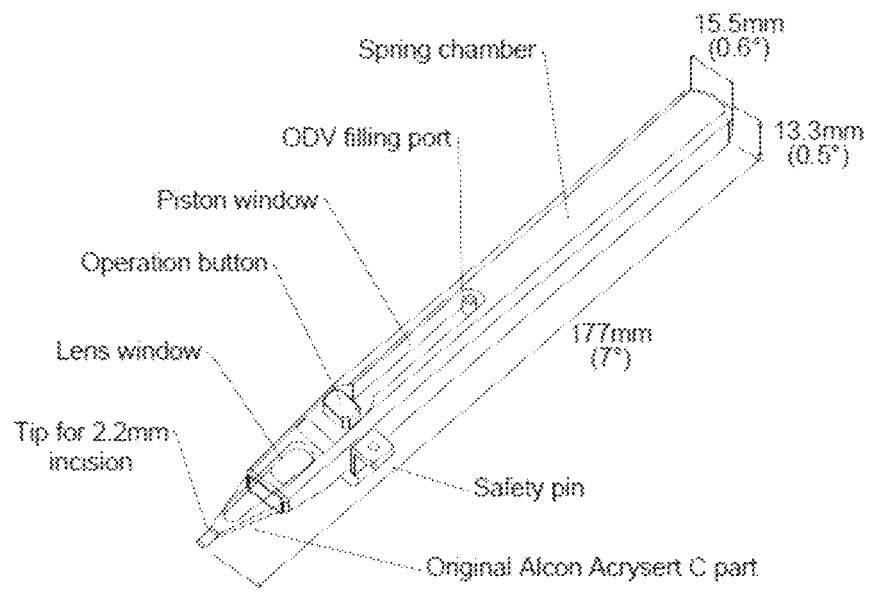
FIG. 1 is a perspective view of the first embodiment of the IOL inserter of the invention.
Figure 2:
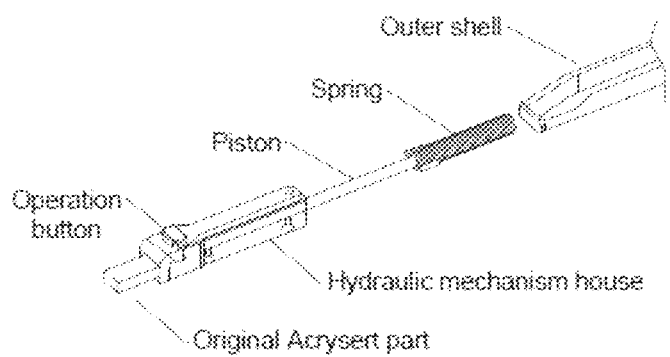
FIG. 2 is a partial view of FIG. 1 showing the interior of the IOL inserter of the first embodiment of the invention.
Figure 3:
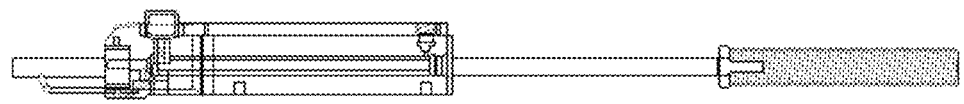
FIG. 3 is a partial view of FIG. 1 showing the interior of the IOL inserter of the first embodiment of the invention.
Figure 4:
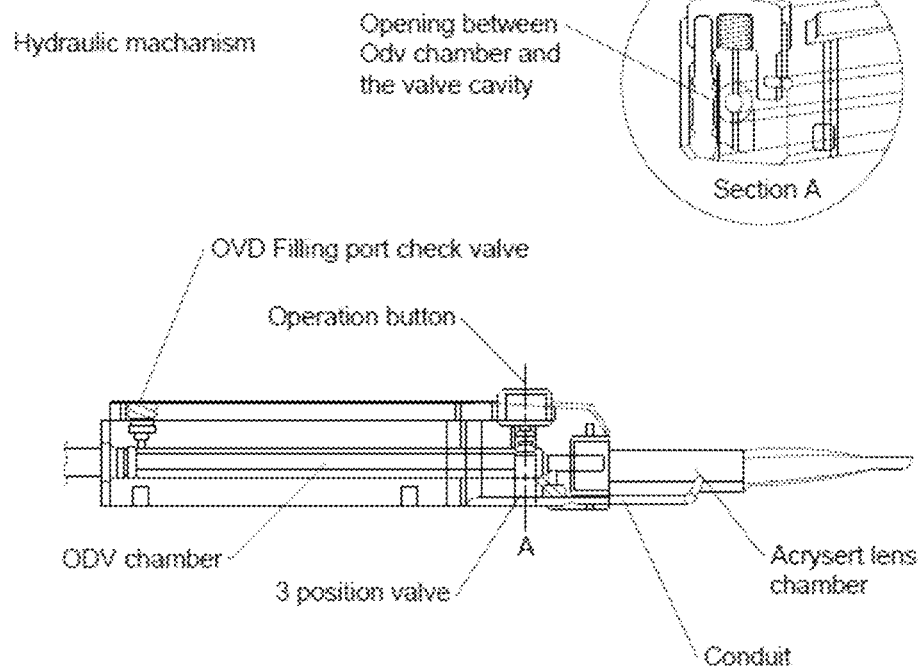
FIG. 4 is a partial view of FIG. 1 showing the interior of the IOL inserter of the first embodiment of the invention.
Figure 5:
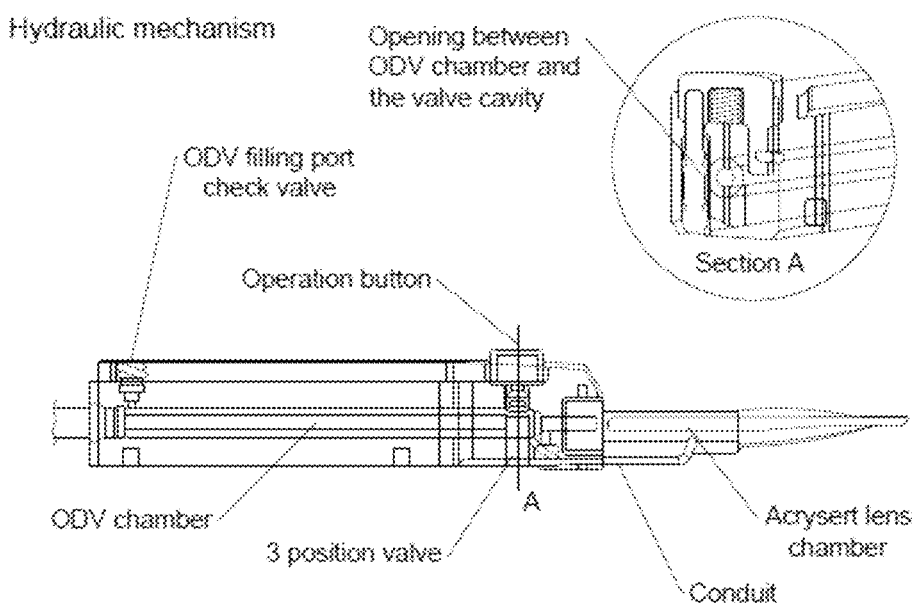
FIG. 5 is a partial view of FIG. 1 showing the interior of the IOL inserter of the first embodiment of the invention.
Figure 6:
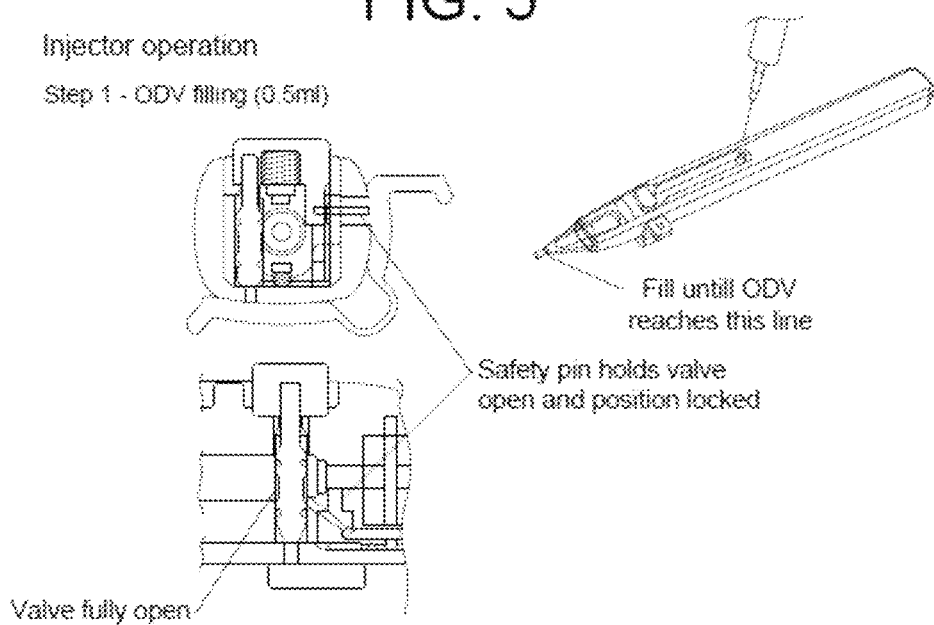
FIG. 6 is a partial view of FIG. 1 showing the interior of the IOL inserter of the first embodiment of the invention with the OVD chamber filled with OVD via the OVD filling port check valve.
Figure 7:
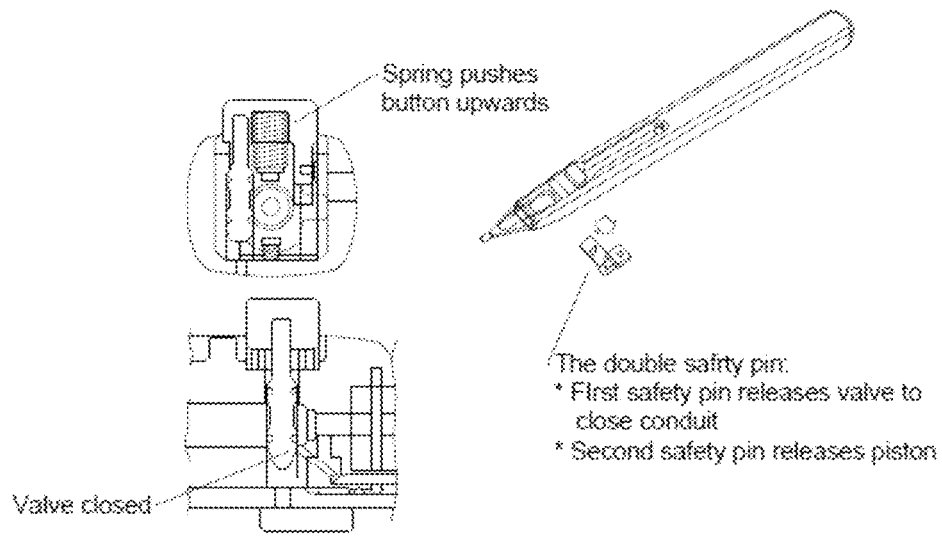
FIG. 7 is a partial view of FIG. 1 showing the interior of the IOL inserter of the first embodiment of the invention with removal of the safety pin.
Figure 8:
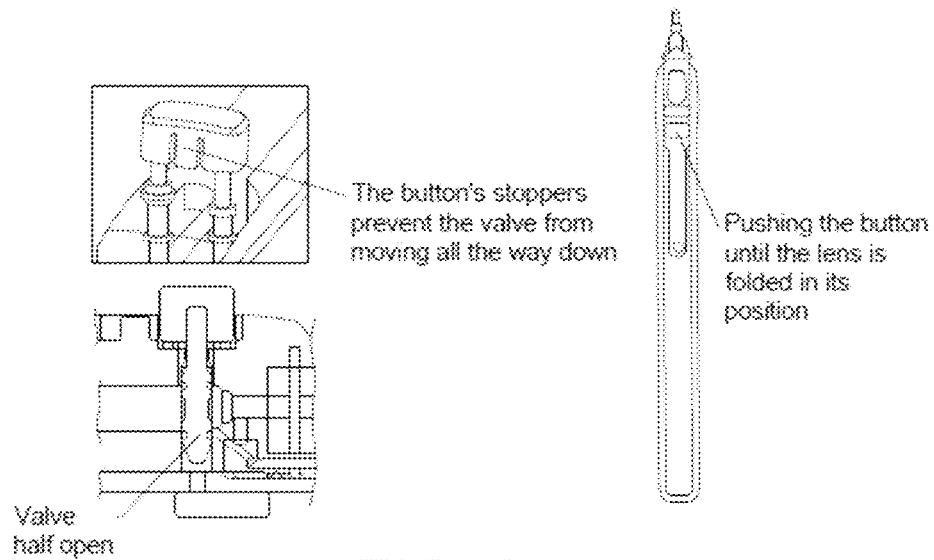
FIG. 8 is a partial view of FIG. 1 showing the interior of the IOL inserter of the first embodiment of the invention upon depressing the operation button to partially open the valve.
Figure 9:
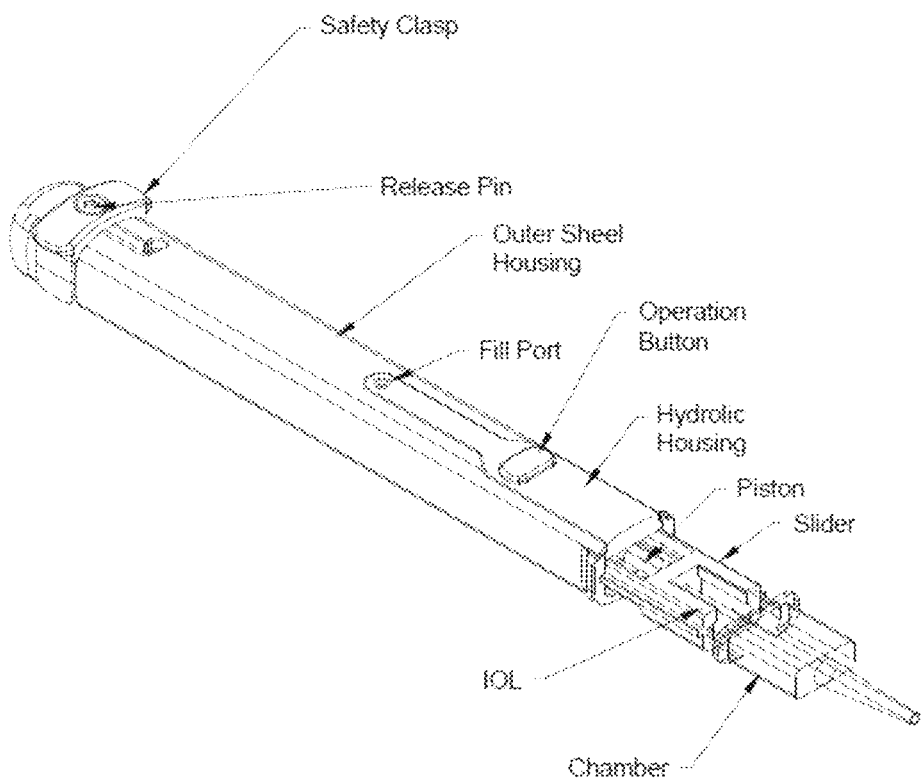
Figure 10:
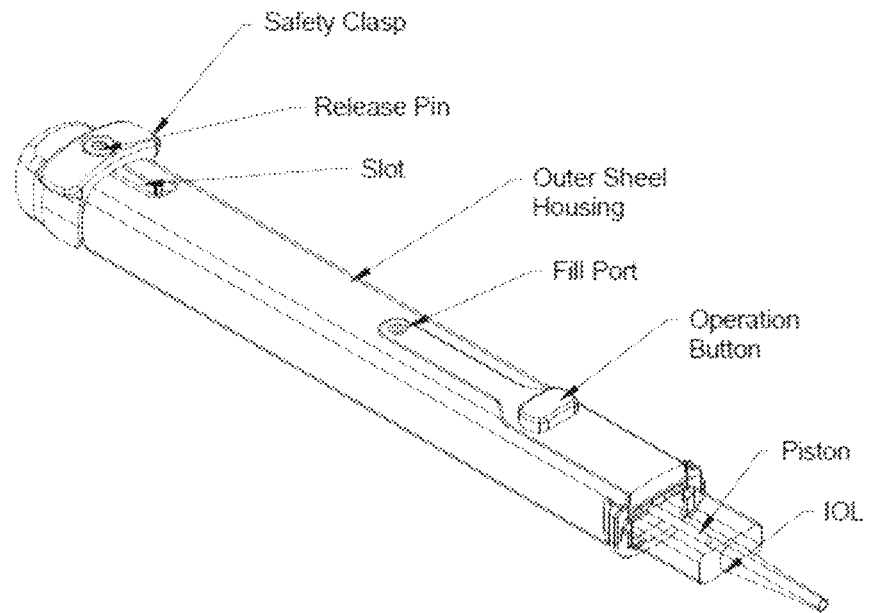
FIG. 10 is a perspective view of the second embodiment of the IOL inserter of the invention showing the slider pushed inwardly into the proximal end of the outer shell housing.
Figure 11:
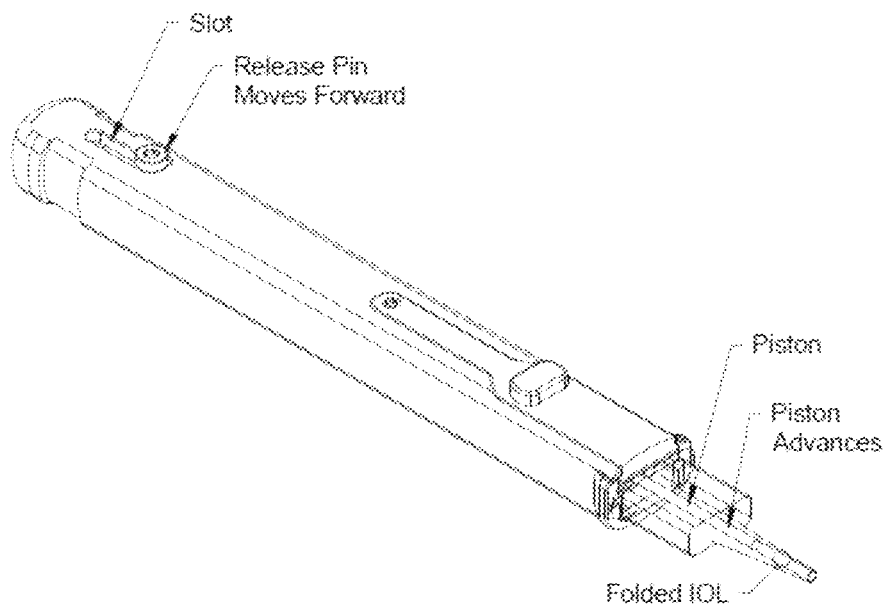
FIG. 11 is a perspective view of the second embodiment of the IOL inserter of the invention showing the release pin moved slightly forward.
Figure 12:
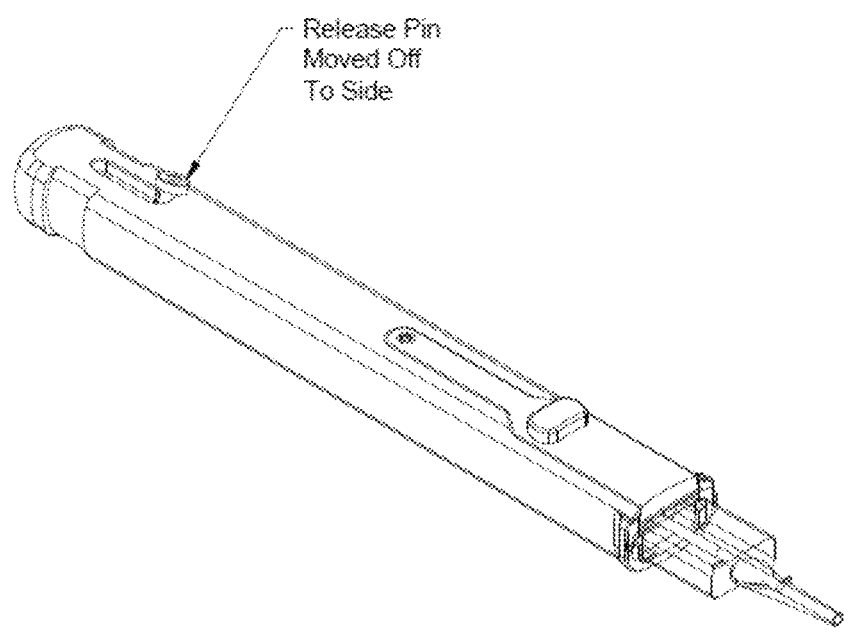
FIG. 12 is a perspective view of the second embodiment of the IOL inserter of the invention showing the release pin moved off to the side.
Figure 13:
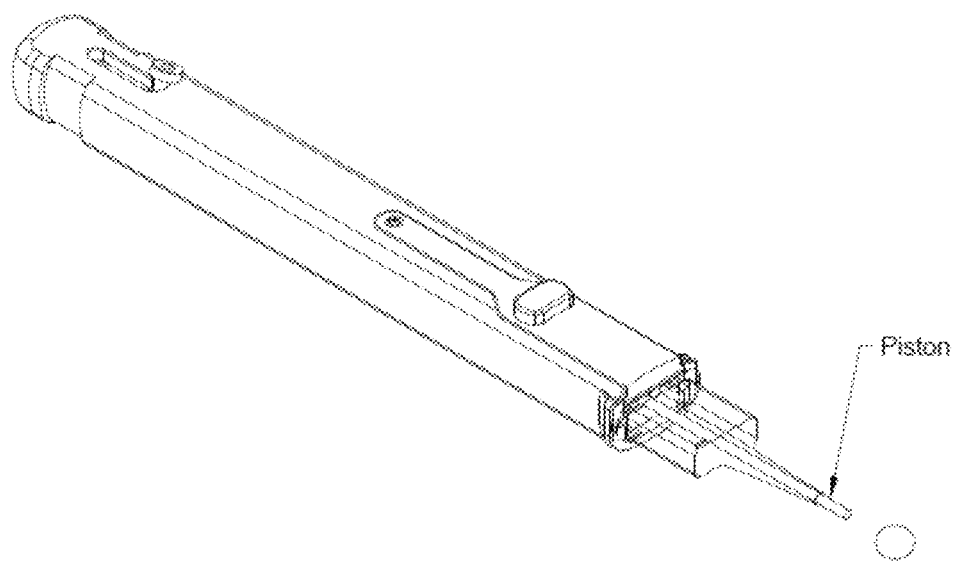
FIG. 13 is a perspective view of the second embodiment of the IOL inserter of the invention showing the delivery of the lens from the IOL.

A more detailed description the first embodiment of the IOL inserter of the invention summarized above in FIGS. 1-8, is reflected in the mechanical drawings of FIGS. 14-16, with the modification of redesigning the safety pin as a safety clasp positioned to the rear of the inserter as more particularly described below.

Referring to FIGS. 14-16, the first embodiment of the IOL inserter 10 of the invention comprises a hydraulic housing 12 positioned within an outer shell housing 14 and secured by screws 15. The hydraulic housing 12 is operatively connected to an IOL cartridge 16 pre-loaded with an IOL 18 for delivery into a person's eye upon removal of a safety clasp 20 and depressing of an operation button 22.

As better shown in FIG. 15 A-A, a hydraulic piston 24 is positioned within a longitudinal bore 26 in the hydraulic housing 12. The piston 24 includes a smaller-diameter portion 28 extending through the longitudinal bore 26 and a larger-diameter portion 30 extending into a longitudinal cylinder 32 formed in the outer shell housing 14. Being smaller in diameter than the lumen of the longitudinal bore 26, the smaller-diameter portion 28 defines an annular hydraulic chamber 31.

The distal end of the piston 24 includes a piston head 34 dimensioned to slide within the longitudinal cylinder 32. A high pressure compression spring 36 is entrained between the piston head 34 and the rear wall 38 of the longitudinal cylinder 32 to constantly urge the piston 24 forwardly.

The safety clasp 20 comprises resilient arms 40 that removably grasp around the rear of the outer shell housing 14. The safety clasp 20 includes an inwardly extending safety pin 42 that extends through a pin opening 44 in the outer shell housing 14 to block the forward movement of the piston head 34 until removed.

The hydraulic housing 12 includes a fill port 46 connected in fluid communication with the hydraulic chamber 31. The fill port 46 includes an elastomeric stopper 48 capable of being pierced by a hypodermic needle of a syringe filled OVD fluid. The hydraulic chamber 31 may be filled with OVD fluid by injection from the OVD-filled syringe. Once filled and the hypodermic needle is removed, the stopper 48 fully closes to prevent any leakage of OVD fluid from the chamber 31.

A first O-ring 50 is positioned about the larger-diameter portion 30 of the piston 24 close to the transition to the smaller-diameter portion 28. The first O-ring 50 functions to seal against the lumen of the longitudinal bore 26 as the piston 24 moves forwardly, thereby forcing the OVD fluid within the hydraulic chamber 31 through the operation button 22 (described hereinafter). It is noted that the front (proximal) end of the longitudinal bore 26 steps down to a reduced diameter equal to that of the small-diameter portion 28 of the piston 24. A second O-ring 52 is positioned at the step 54 to sealingly engage around the smaller-diameter portion 28 of the piston 24 to prevent OVD fluid in the hydraulic chamber 31 from leaking therethrough.

As best shown in FIGS. 15B-B and 16H-H, a first bleed channel 56 extends from the hydraulic chamber 31 to a vertically extending valve cylinder 58. A second bleed channel 60 extends from the valve cylinder 58 to the IOL cartridge 16. The second bleed channel 60 is at a higher level than the first bleed channel 56.

A valve element 62 is positioned within the valve cylinder 58. Upper and lower O-rings 62U and 62L are positioned on the valve element 60 and spaced apart along the length thereof such that when the O-rings 62 straddle the bleed channels 56 and 60, fluid flow is established between the hydraulic chamber 31 and the IOL cartridge 16 (see FIG. 15B-B). When the valve element 62 is positioned such that the lower O-ring 62L is above the first bleed channel 56, fluid flow from the hydraulic chamber 31 and the IOL cartridge 16 is blocked.

The operation button 22 is connected to the valve element 62. A spring 64 is entrained underneath the button 22 and a notch 66 in the hydraulic housing 12 to constantly urge the button upwardly. However, while the IOL cartridge 16 inserted into the hydraulic housing 12 but not fully seated, the position of the button 22 is kept downwardly (i.e. open) by a catch so that the OVD fluid may flow from the hydraulic chamber 31 into the IOL cartridge 16 to fill the same. When the IOL cartridge 16 is fully inserted and seated in the hydraulic housing 12, the button 22 is released and allowed to move upwardly to block (i.e., close) the fluid flow from the first bleed channel 56 to the second bleed channel 60.

The ergonomic design of the IOL inserter 10 allows for one-handed operation by the surgeon. Depressing of the surgeon's finger on the button 22 against the resiliency of spring 64 moves the valve element 62 downwardly to the point where the O-rings 62U and 62L straddle the first bleed channel 56. OVD fluid is thus bled from the hydraulic chamber 31 and into the IOL cartridge. As the OVD fluid is bled from the chamber 31, the high pressure of the spring 36 forces the piston 24 forwardly in a smooth and deliberate speed. As the piston 24 moves forward, the tip 68 of the small-diameter portion 38 extends further into the IOL cartridge 16 to deliver the IOL 18 into the patient's eye. At any point during the forward travel of the piston 24, the surgeon may release the button 22 whereupon spring 64 returns the button 22 to its upward position and valve element 62 moves to its closed position (see FIG. 16H-H).

Second Embodiment

A more detailed description the second embodiment of the IOL inserter 12 of the invention summarized above in FIGS. 9-13, is reflected in the mechanical drawings of FIGS. 14-28, with several modifications. It is noted that components in common with the first embodiment are numerically labeled with corresponding numbers prefixed by 100s or 200s. For example, the IOL inserter 10 of the first embodiment is labeled with numeral "10" whereas the IOL inserter of the second embodiment is correspondingly labeled with numeral "110." It is noted that the description of the second embodiment 110 is largely the same as the first embodiment 10 and is therefore replicated, except of course where the second embodiment 110 is structurally different.

Referring to FIGS. 14-19, the first embodiment of the IOL inserter 110 of the invention comprises a hydraulic housing 112 positioned within an outer shell housing 114 and secured by screws 115. The hydraulic housing 112 is operatively connected to an IOL cartridge 116 pre-loaded with an IOL 118 for delivery into a person's eye upon removal of a safety clasp 120 and depressing of an operation button 122.

As better shown in FIGS. 18 A-A, a hydraulic piston 124 is positioned within a longitudinal bore 126 in the hydraulic housing 112. The piston 124 includes a smaller-diameter portion 128 extending through the longitudinal bore 126 and a larger-diameter portion 130 extending into a longitudinal cylinder 132 formed in a piston housing 170 positioned in the outer shell housing 114. Being smaller in diameter than the lumen of the longitudinal bore 126, the smaller-diameter portion 128 defines an annular hydraulic chamber 131.

The distal end of the piston 124 includes a piston head 134 dimensioned to slide within the longitudinal cylinder 132. A high pressure compression spring 136 is entrained between the piston head 134 and the rear wall 138 of the longitudinal cylinder 132 to constantly urge the piston 124 forwardly.

The safety clasp 120 comprises resilient arms 140 that removably grasp into corresponding depressions 176 formed on opposing sides of the rear of the outer shell housing 114. A separate inwardly extending safety pin 172 extends through a pin opening 174 in the center of the clasp 120 and through a J-shaped slot 180 formed in the outer shell housing 14 and is permanently connected to the piston housing 170 by threads 178. It is noted that only upon removal of the clasp 120 is the safety pin 172 allowed to move within the J-shaped slot 180. Because the safety pin 172 is permanently connected to the piston housing 170, movement of the piston housing 170 is defined by the configuration of the J-shaped slot 180 to first move longitudinally outwardly and then rotationally (compare FIGS. 11 and 12).

The rearward (distal) end of the piston housing 170 comprises a boss 182 that extends into rear of the outer shell housing 114. A compression spring 184 is positioned concentrically over the boss 182. As shown in FIG. 18 J-J, inwardly extending guide fingers 186 center the boss 182 and spring 184 within the rear of the outer shell housing 114. Being entrained between the piston housing 170 and the rear of the outer shell housing 114, spring 184 constantly urges the piston housing 170 forwardly. When the safety clasp 120 is removed, the safety pin 172 is freed and is allowed to move within J-slot 180. Spring 184 therefore moves the piston housing 170 forwardly a short distance equal to the length of the long leg of the J-slot 180. Then, when the safety pin 172 is rotated over into the short leg of the J-slot 180, the piston housing 170 correspondingly rotates in the same direction by the same rotational degree.

Rotational movement of the piston housing 170 while moving along the length of the long leg of the J-slot 180 as described above, is also prevented by means of opposing ears 188 emanating from the rear of the piston housing 170 that ride in a rails 190 (see FIG. 18 L-L).

Figure 20:
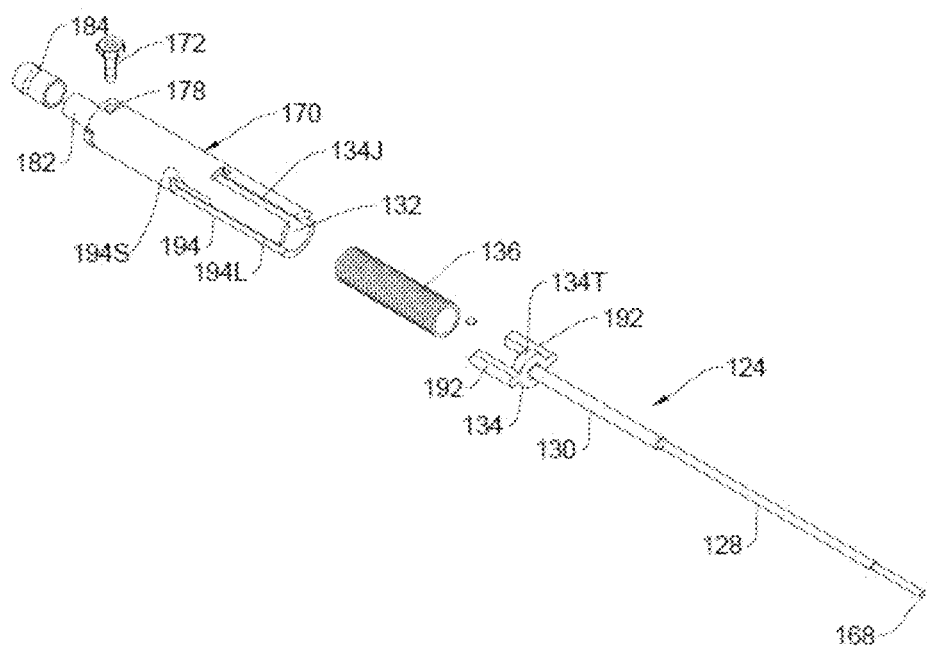
Figure 21:
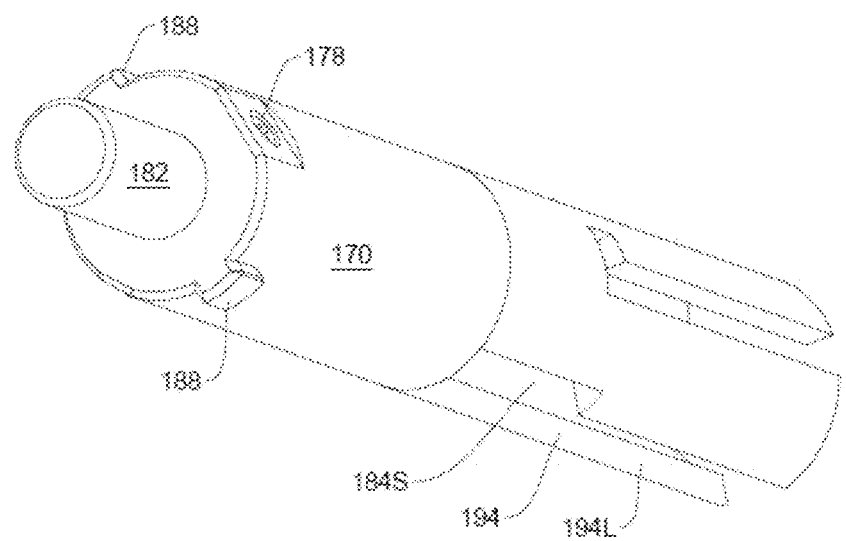
FIGS. 21-23 are partial exploded interior views of the second embodiment of the IOL inserter of the invention showing the interior components thereof.
Figure 22:
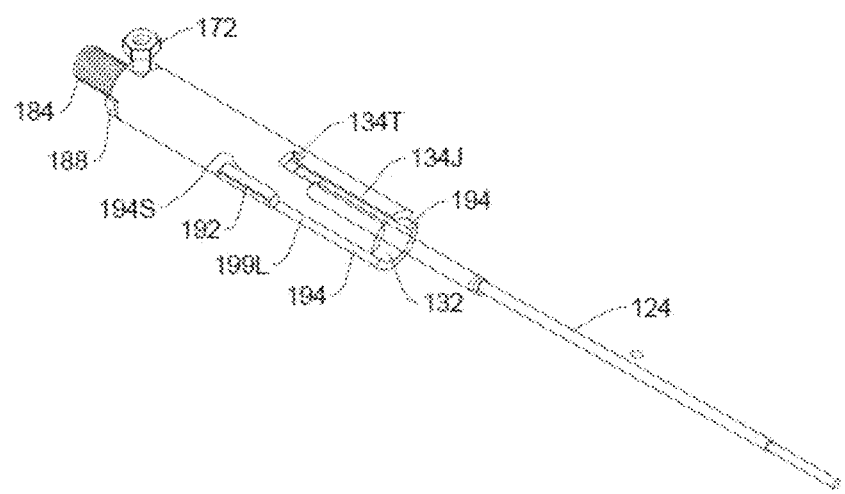

Referring to FIGS. 20-22, the head 134 of the piston 124 comprises opposing parallel arms 192 extending longitudinally from the opposing sides of the head 134. The arms 192 are dimensioned to longitudinally slide into the long legs 194L of corresponding J-slots 194 formed in opposing sides of the piston housing 170. The length of the arms 192 are dimensioned relative to the short leg 194S of the J-slots 194 to fit therein when the piston housing 170 is rotated. As shown in FIG. 18 K-K, the width of each of the arms 192 is greater that the depth of the J-slot 194 such that they protrude beyond the outer periphery of the piston housing 170 to ride in corresponding rails 196 extending inwardly from the inside of the outer shell housing 14, thereby preventing any rotational movement of the piston 24.

It is noted that in its at rest position as shown in FIG. 22, the arms 192 are engaged into the short legs 194S and therefore longitudinal movement of the piston 124 relative to the piston housing 170 is prevented. However, as noted above, as the safety pin 172 is rotated into the short leg of the J-slot 180, the piston housing 170 correspondingly rotates in the same direction by the same rotational degree. Because the piston 194 is itself prevented from rotation due to rails 196, once the piston housing 170 is rotated as the safety pin 172 is rotated into the short leg of the J-slot 180, the arms 192 rotate out of the short leg 194S into the long leg 190L of the J-slot 190, thereby allowing the high pressure compression spring 136 to forcibly urge the piston 124 forwardly.

Similar to the function of the J-slot 180, the head 134 of the piston 124 may include opposing radial tabs 134T that extend into another J-slot 134J in the piston housing 170 to provide addition support for keeping the spring 136 compressed until the piston housing 170 is rotated by the safety pin 172.

The hydraulic housing 112 includes a fill port 146 connected in fluid communication with the hydraulic chamber 131. The fill port 146 includes an elastomeric stopper 148 capable of being pierced by a hypodermic needle of a syringe filled OVD fluid. The hydraulic chamber 131 may be filled with OVD fluid by injection from the OVD-filled syringe. Once filled and the hypodermic needle is removed, the stopper 148 fully closes to prevent any leakage of OVD fluid from the chamber 131.

A first O-ring 150 is positioned about the larger-diameter portion 130 of the piston 124 close to the transition to the smaller-diameter portion 28. The first O-ring 150 functions to seal against the lumen of the longitudinal bore 126 as the piston 124 moves forwardly, thereby forcing the OVD fluid within the hydraulic chamber 131 through the operation button 122 (described hereinafter). It is noted that the front (proximal) end of the longitudinal bore 126 steps down to a reduced diameter equal to that of the small-diameter portion 128 of the piston 124. A second O-ring 152 is positioned at the step 154 to sealingly engage around the smaller-diameter portion 128 of the piston 124 to prevent OVD fluid in the hydraulic chamber 131 from leaking therethrough.

As best shown in FIGS. 18B-B and 19H-H, a first bleed channel 156 extends from the hydraulic chamber 131 to a vertically extending valve cylinder 158. A second bleed channel 160 extends from the valve cylinder 158 to the IOL cartridge 116. The second bleed channel 160 is at a higher level than the first bleed channel 156.

A valve element 162 is positioned within the valve cylinder 158. Upper and lower O-rings 162U and 162L are positioned on the valve element 60 and spaced apart along the length thereof such that when the O-rings 162 straddle the bleed channels 156 and 160, fluid flow is established between the hydraulic chamber 131 and the IOL cartridge 116 (see FIG. 18B-B). When the valve element 162 is positioned such that the lower O-ring 162L is above the first bleed channel 156, fluid flow from the hydraulic chamber 131 and the IOL cartridge 116 is blocked.

Figure 23:
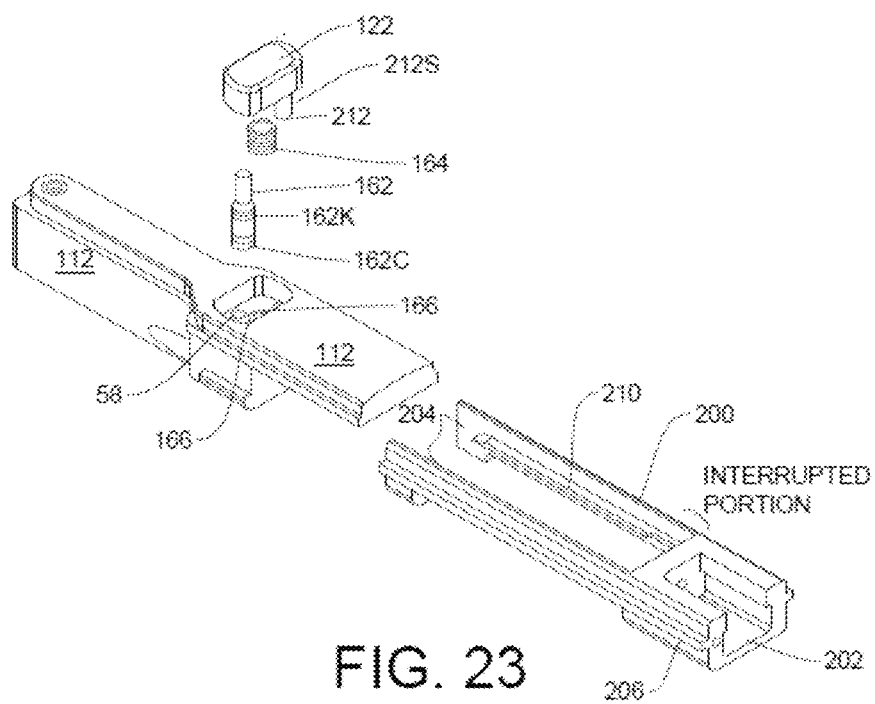

As best shown in FIG. 23, the operation button 122 is connected to the valve element 162. A spring 164 is entrained underneath the button 122 and a notch 166 in the hydraulic housing 112 to constantly urge the button 122 upwardly.

The second embodiment of the IOL injector 110 of the invention includes a slider 200 that interfaces the IOL cartridge 116 to the inserter 110. As shown in FIG. 23, the slider comprises a front receptacle 202 adapted to receive the desired IOL cartridge 116 such as the Abbott's Tecnis 1-Piece Aspheric IOL identified above. FIG. 9A represents Abbott's instructions for use for its IOL cartridge.

As better shown in FIG. 18 M-M, the slider 200 comprises a pair of rearwardly-extending parallel arms 204 having outer rails 206 that engage into corresponding longitudinal slots 208 formed on the inside sides of the outer shell housing 114.

Referring to FIG. 23, the arm 204 on the opposite side of the valve element 62 comprises an interrupted inside rail 210 that fits into a longitudinal slot in the leg 212 of the button 22 to catch (i.e., hold) it in its downward, open position (FIG. 16 H-H) allowing OVD fluid to flow into the IOL cartridge 16.

Figure 24:
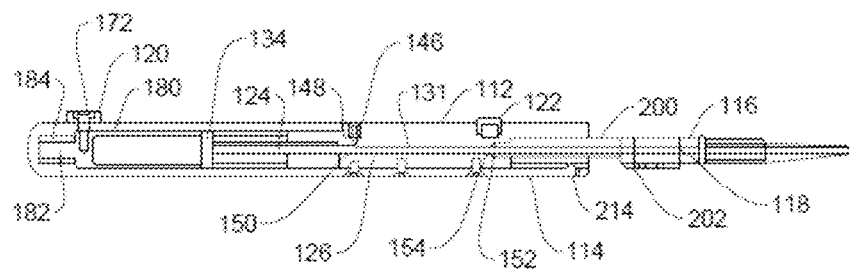
FIGS. 24-28 are longitudinal cross-sectional views of the second embodiment of the IOL inserter of the invention showing the operational sequence thereof.
Figure 25:
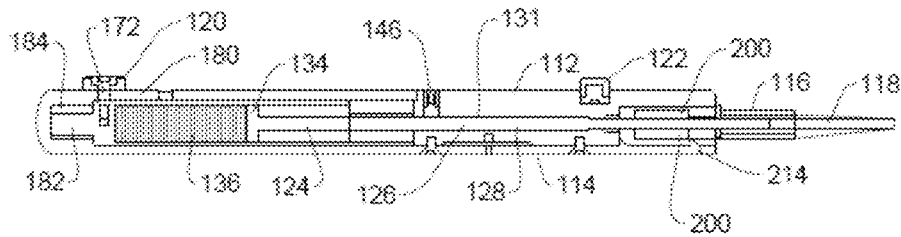

Once the IOL 18 is loaded into the IOL cartridge 116 and the cartridge 116 snapped into the slider 200 (FIG. 24), the slider 200 may be pushed fully inward and held into position by a resilient catch 214 formed in the bottom of the outer shell housing 14 (FIG. 25). Once the slider 200 is snapped into position by catch 214, leg 212 moves over the interrupted part of the rail 210 and the leg 212 and hence the button 122 and valve element 162 move upwardly to its closed position.

Accordingly, while the IOL cartridge 116 inserted into the slider 200 but not fully seated, the position of the button 122 is kept downwardly (i.e. open) so that the OVD fluid may flow from the hydraulic chamber 131 into the IOL cartridge 116 to fill the same (FIG. 24). When the IOL cartridge 16 is fully inserted and seated in the hydraulic housing 112, the button 122 is allowed to move upwardly to block (i.e., close) the fluid flow from the first bleed channel 156 to the second bleed channel 160 (FIG. 25).

The ergonomic design of the IOL inserter 10 allows for one-handed operation by the surgeon. Depressing of the surgeon's finger on the button 22 against the resiliency of spring 64 moves the valve element 62 downwardly to the point where the O-rings 62U and 62L straddle the first bleed channel 56. OVD fluid is thus bled from the hydraulic chamber 31 and into the IOL cartridge. As the OVD fluid is bled from the chamber 31, the high pressure of the spring 36 forces the piston 24 forwardly in a smooth and deliberate speed. As the piston 24 moves forward, the tip 68 of the small-diameter portion 38 extends further into the IOL cartridge 16 to deliver the IOL 18 into the patient's eye. At any point during the forward travel of the piston 24, the surgeon may release the button 22 whereupon spring 64 returns the button 22 to its upward position and valve element 62 moves to its closed position (see FIG. 16H-H).

FIGS. 24-28 respectfully correspond to FIGS. 9-13 showing the start-to-finish use of the second embodiment of the IOL inserter 110.

In FIG. 24, the IOL cartridge 116, loaded with an OVD-wetted IOL 118, has been snapped into the receptacle 202 of the slider 200 and the slider 200 has been partially inserted into the outer shell housing 114. In this position, the valve element 162 is held open by means of the interrupted rail 210. The surgical assistant fills the hydraulic chamber 131 with OVD via the fill port 146 with sufficient excess fluid flowing into the IOL cartridge 116 per the manufacturer's instructions for use.

As shown in FIG. 25, the slider 200 is pushed fully inward and snapped and held in position by the catch 214. In this position, valve element 162 closes because of the interruption in the interrupted rail 210.

Figure 26:
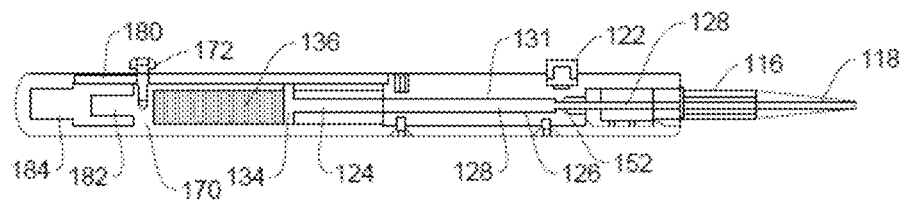

As shown in FIG. 26, when surgical assistant removes the safety clasp 120, the safety pin 172 (and therefore piston housing 170 and piston 124) move forwardly the distance of the long portion of the J-slot 180 by means of spring 184. This forward movement of the piston 124 advances the smaller-diameter portion 128 of the piston 124 further into the IOL cartridge 116 to advance and hence fold the IOL 118 further into the delivery portion of the cartridge 116.

Figure 27:
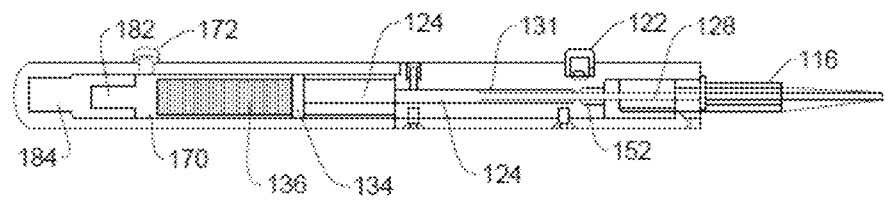

As shown in FIG. 27, the surgical assistant rotates the safety pin 172 whereupon the piston housing 170 also rotates to disengage the arms 192 of the piston 124 from the of the shorter legs 194S of the J-slots 194. This releases the full force of the high compression spring 136 against the head 134 of the piston 124; however, the piston 124 does not move forward because the valve element 162 is closed, trapping the OVD fluid in the hydraulic chamber 131. The IOL inserter 110 is now ready and the surgical assistant hands it to the surgeon.

Figure 28:
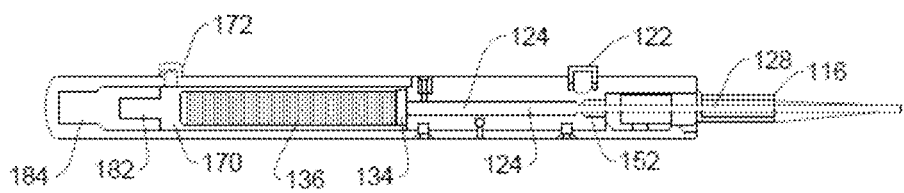
Figure 29:
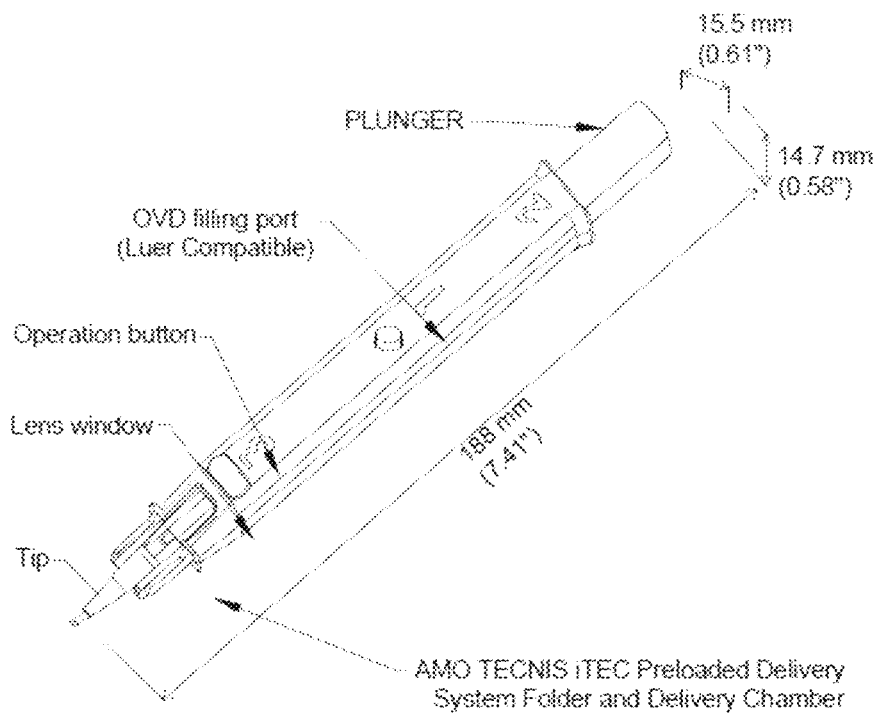
FIG. 29 is a perspective view of the third embodiment of the IOL inserter of the invention.
Figure 30:
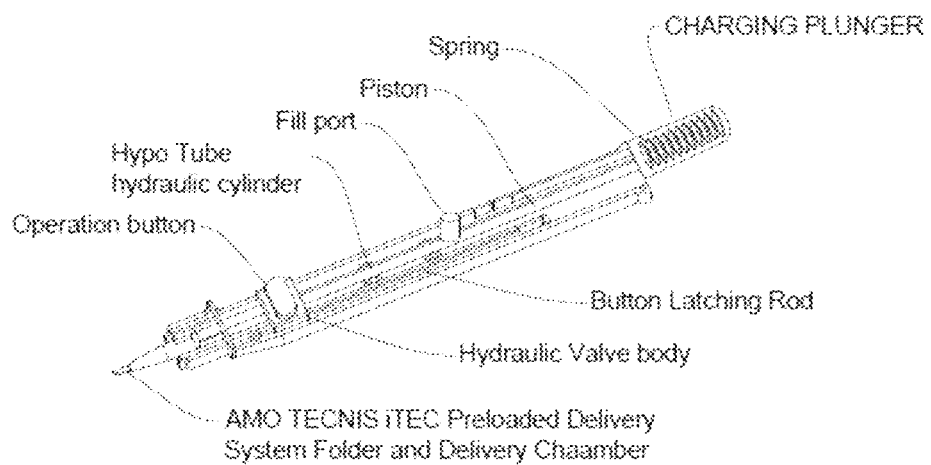
FIG. 30 is a partial view of FIG. 29 showing the interior components of the IOL inserter
Figure 31:
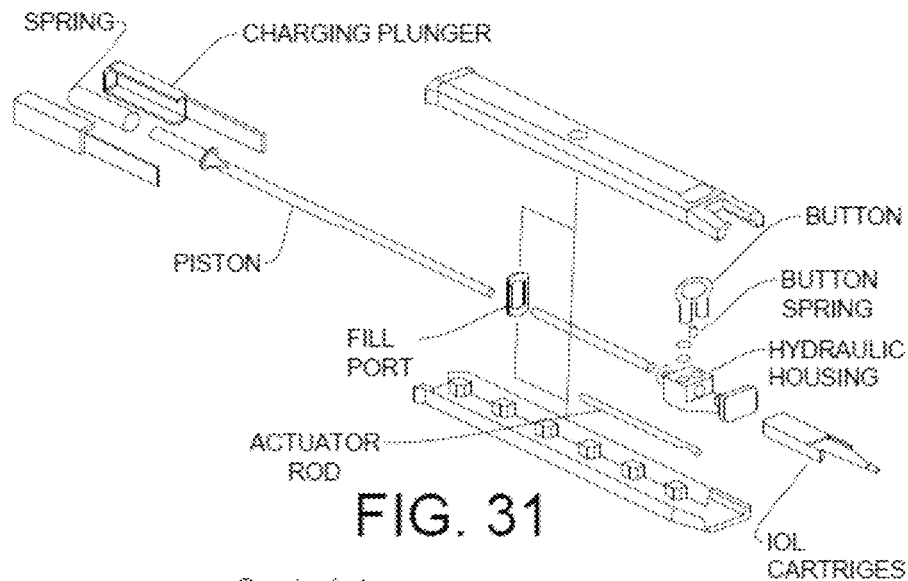
FIG. 31 is an exploded perspective view of FIG. 29.
Figure 33:
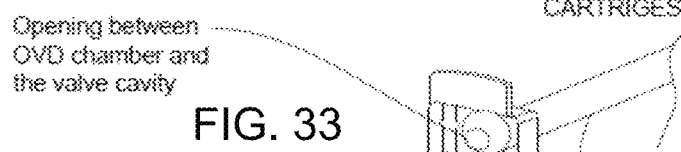
Figure 32:
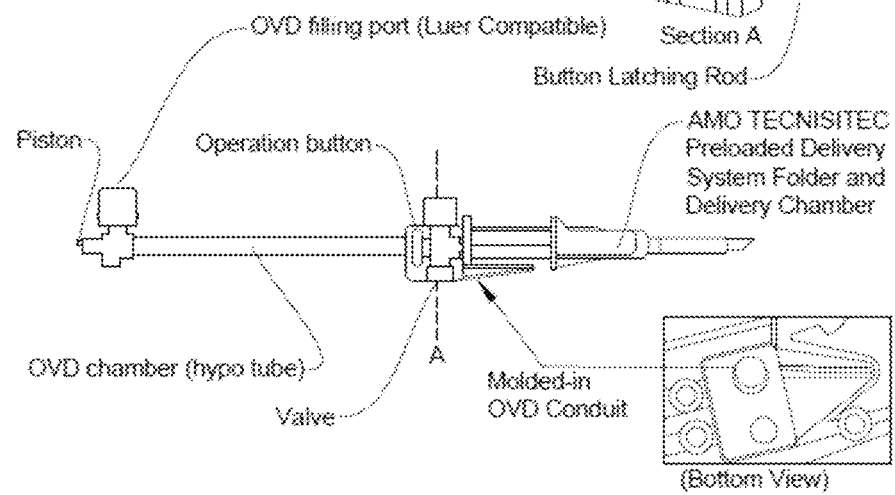
FIG. 32 is a perspective view of FIG. 29 showing the charging plunger activated.
Figure 34:
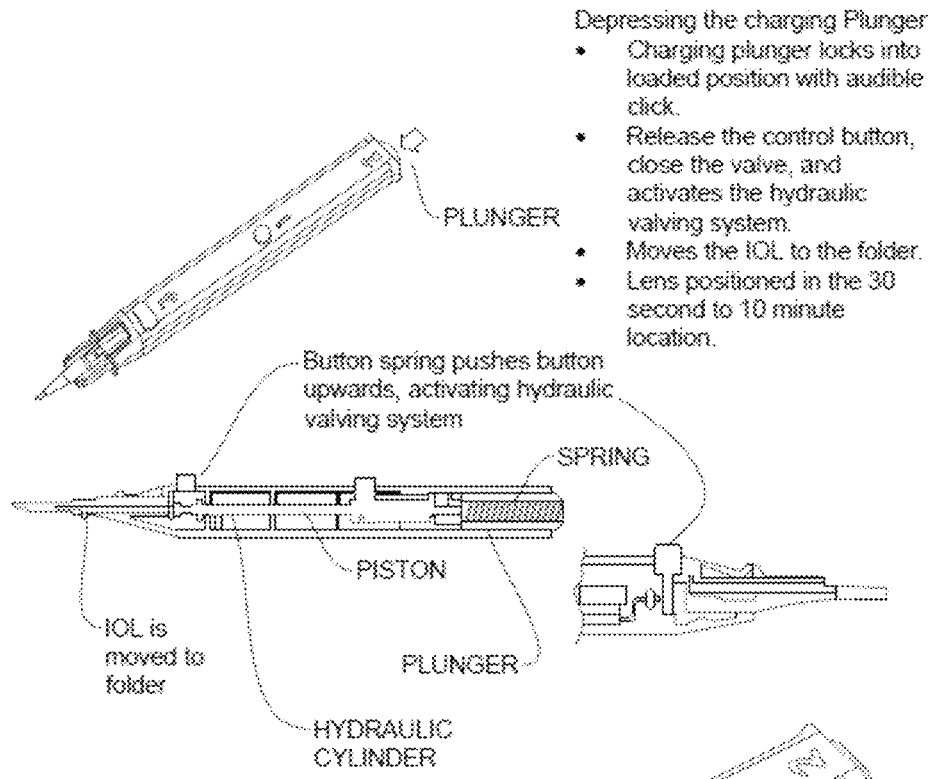
FIG. 34 partial view of FIG. 29 showing the interior components of the IOL inserter.
Figure 35:
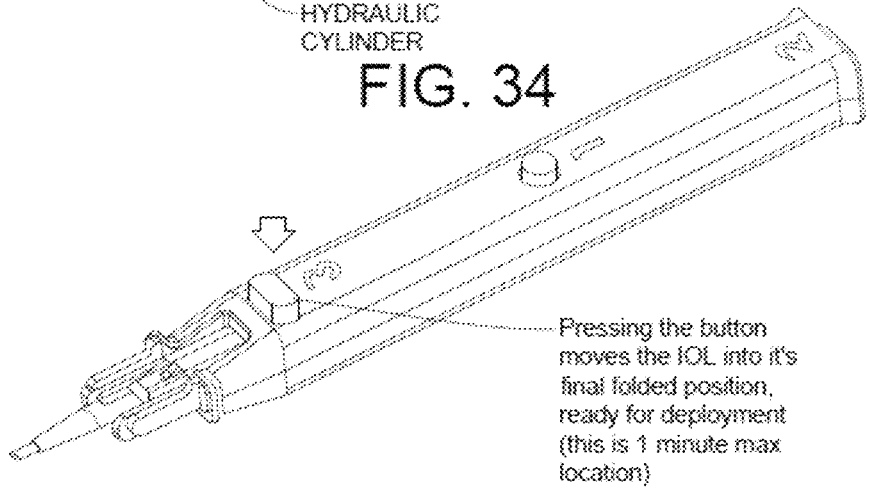
FIGS. 35 and 36 are perspective views of FIG. 29 showing the depressed button.
Figure 36:
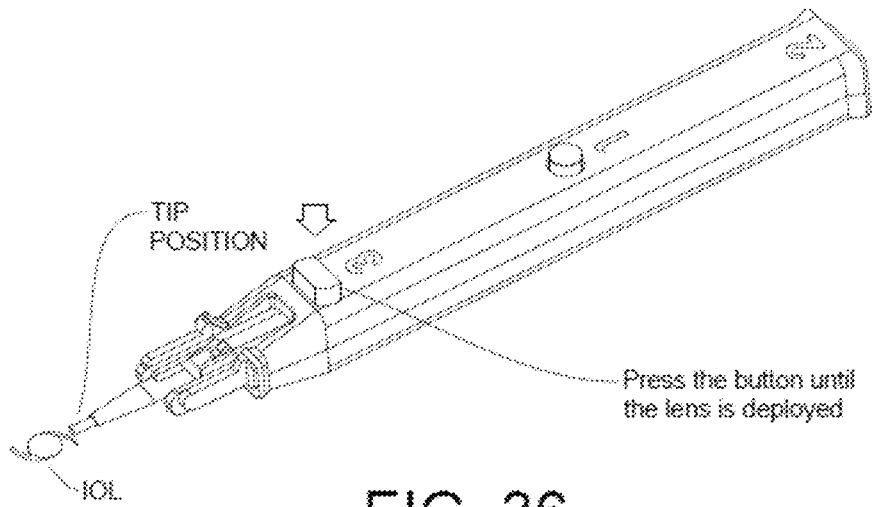
Figure 37:
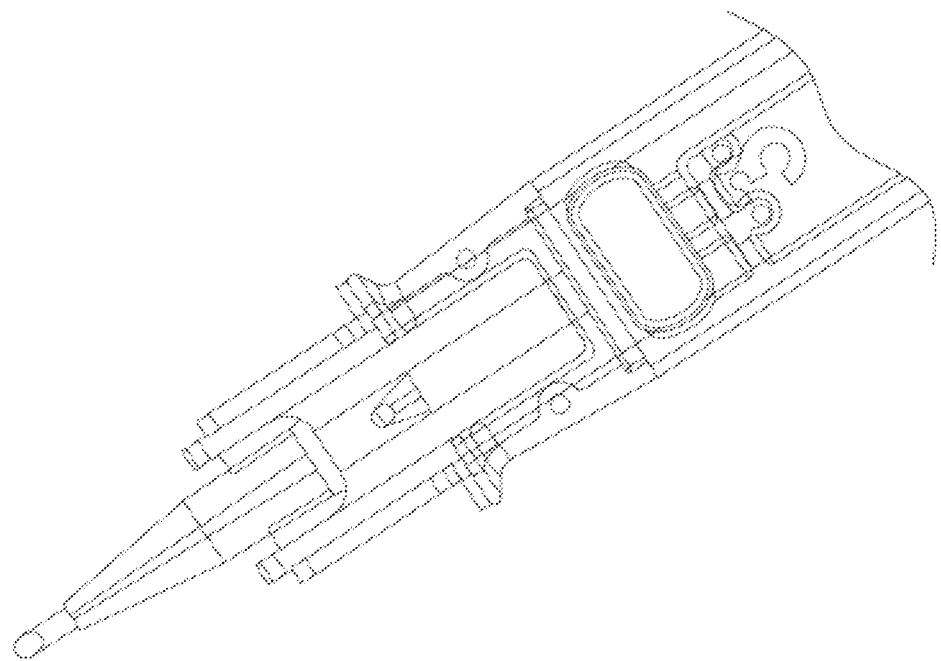
FIG. 37 is a close-up view of Abbott's IOL cartridge for its Tecnis 1-Piece Aspheric IOL.

As shown in FIG. 28, in the hands of the surgeon, depressing of the operation button 122 slowly and controllably bleeds OVD fluid from the hydraulic chamber 131, whereupon the piston 124 moves steadily forwardly without pulsating or overshooting, to safely and deliberately deliver the IOL 118 into the patient's eye under precise control of the surgeon's finger.

Third Embodiment

A more detailed description the third embodiment of the IOL inserter 312 of the invention summarized above in FIGS. 29-37, is reflected in the mechanical drawings of FIGS. 38-55. It is noted that components in common with the first embodiment are numerically labeled with corresponding numbers prefixed by 300s and 400s. For example, the IOL inserter 10 of the first embodiment is labeled with numeral "10" whereas the IOL inserter of the third embodiment is correspondingly labeled with numeral "310."

Figure 38:
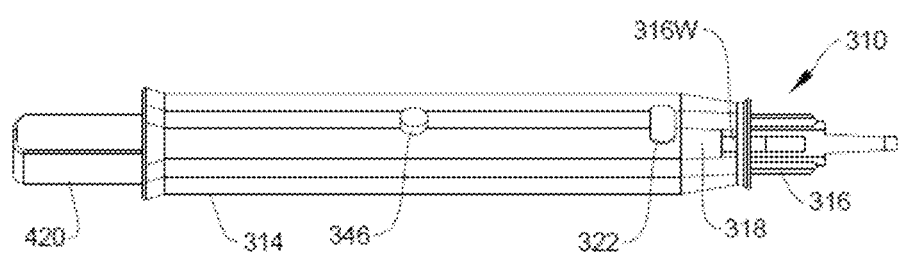
FIG. 38 is a top plan view of the third embodiment of the IOL inserter of the invention.

As shown in FIG. 38, the third embodiment of the IOL inserter 310 comprises an outer shell housing 314 into which is loaded an IOL cartridge 316 having a clear window 316W for visualizing the IOL 318 and OVD fluid therein. The IOL inserter 310 further includes a fill-port 346 for filling with OVD fluid.

Figure 39:
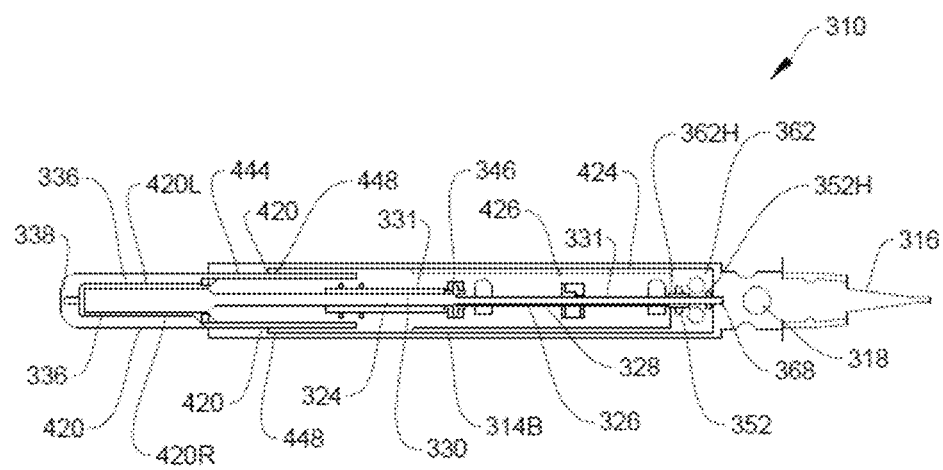
FIG. 39 is a longitudinal cross-sectional view of FIG. 38.

As better shown in FIG. 39, the fill-port 346 is fluidly connected to a hydraulic tube 326 in which is positioned the smaller diameter portion 328 of a hydraulic piston 324. It is noted that leakage about the periphery of the hydraulic tube 326 is precluded by O ring 352 positioned about the forward most end of the tube 326 which seals within the valve housing 362H. The forward end of the hydraulic tube 326 extends into a valve housing 362H and sealed by second O-ring 352. The tip 368 of the piston 324 extends out of the hydraulic tube 326 within the valve housing 362H and extends into the IOL cartridge 316. Another O-ring 362H prevents leakage between the tip 368 and the housing 362H.

Figure 40:
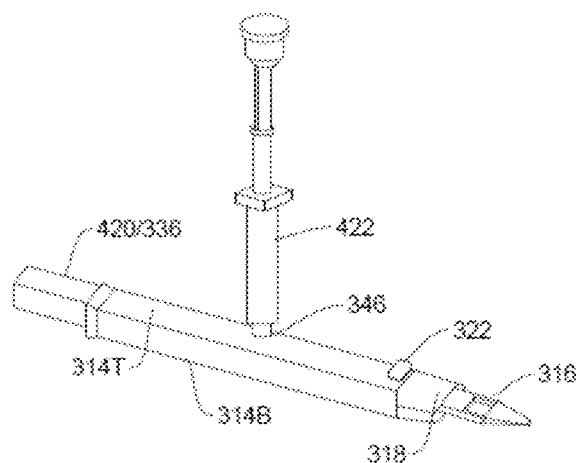
FIGS. 40 and 44 are plan and partial cross-sectional views showing the OVD fluid being injected into the IOL inserter by means of an OVD-filled syringe.

The annular space between the outer surface of the smaller diameter portion 328 of the hydraulic piston 324 and the lumen of the hydraulic tube 326 define a hydraulic chamber 331. As shown in FIG. 40, when OVD fluid is injected into the IOL inserter 310 by means of an OVD-filled syringe 422, the OVD fluid flows through the fill port 346 into the hydraulic chamber 331 and then, as explained later in greater detail, into the valve housing 362H containing the valve 362, through the valve 362 and into the IOL cartridge 316. Valve 362 is similar to the first and second embodiments 62 and 162 and comprises a valve element 362 having upper and lower O-rings 362U and 362L installed within a valve cylinder 358.

Preferably, fill port 346 comprises a Luer fitting. As better shown in FIG. 41, the fill port 346 comprises a generally circular bore 346B. The rearward end 326R of the hydraulic tube 326 is sealingly inserted into the forward portion of the bore at 346B. A first O-ring 350 is positioned in an O-ring slot formed at the juncture between the smaller diameter portion 328 and the larger diameter portion 330 of the piston 324 to form a seal with the rear portion of the bore 346B.

Figure 41:
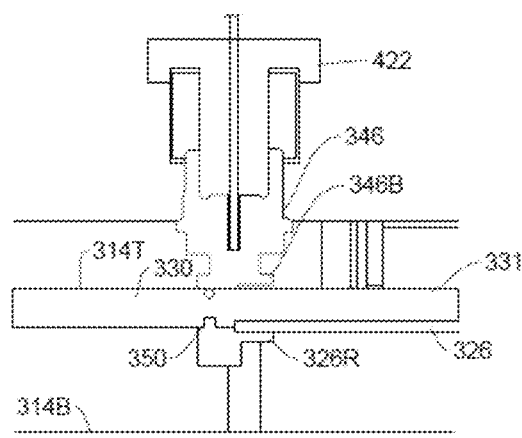
FIG. 41 is an enlarged partial cut-away view of FIG. 39 showing the fluid flowing through the upper portion of the port and into the hydraulic chamber.
Figure 42:
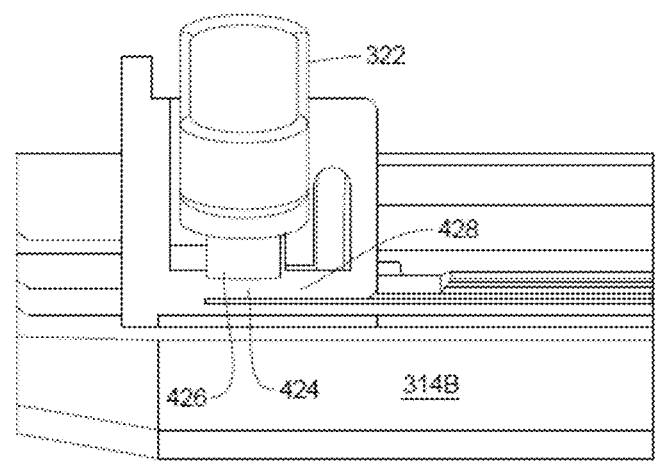
FIGS. 42 and 43 are an enlarged partial cut-away view of FIG. 39 showing the operation button.
Figure 43:
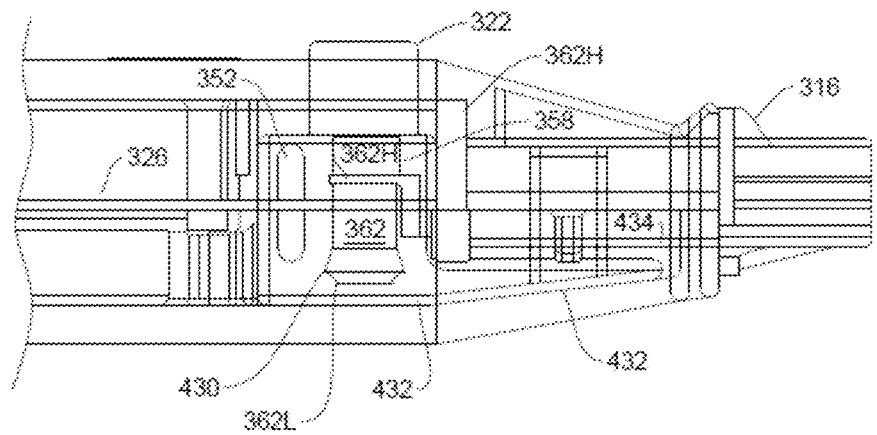
Figure 44:
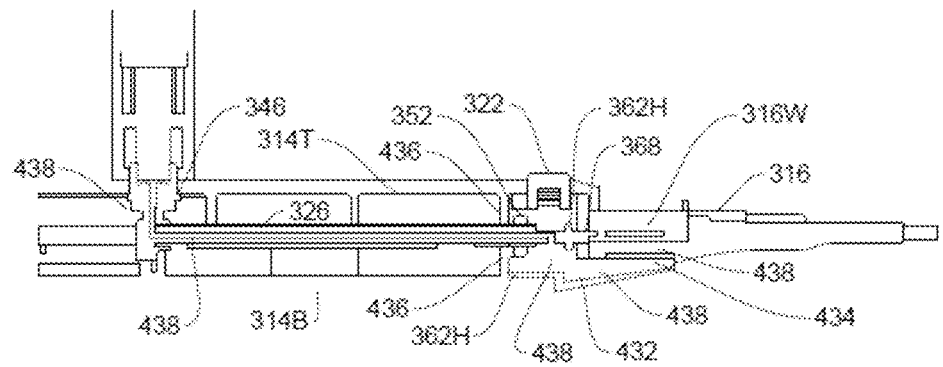

When the OVD-filled syringe is connected to the fill port 346 as shown in FIG. 41, fluid flows through the upper portion of the port 346 and into the hydraulic chamber 331 to fill the same and to then through the valve housing 362H to fill the IOL cartridge 316. After removal of the syringe, and charging of the IOL inserter 310 (described hereafter), the piston 324 moves forwardly whereupon O-ring 350 moves into the rearward end of the hydraulic tube 326, thereby forming a seal therewith.

Returning to FIG. 39, the operation button 322 is operatively connected to the leg 312 and is spring-loaded upwardly by a spring 364. The operation button 322 and hence the valve 362 are held in their "down" or "open" position by means of a latching/unlatching mechanism 410 that fits into a side slot 412S in the leg 312 of the button 322. Functioning similar to the interrupted rail 210 of the second embodiment, the end of the unlatching mechanism 410 includes a cut out portion 428 that allows the valve 362 to move upwardly within the valve cylinder 358 of the valve housing 362H when the mechanism 410 is slid forwardly with the cut out portion 428 in alignment with the slot 412S.

As shown in FIGS. 40-46 illustrating Step 1 of the intended use, so long as the valve element 362 is latched open by the mechanism 410, its lower O ring 362L is positioned in a frustro-conical portion 430FC of a bleed channel 430 where the lower O ring 362L is no longer being sealed inside the circular-cylindrical valve cylinder 358, thereby allowing OVD fluid to bleed around the O ring 362L and into the lower circular-cylindrical portion 430CC of the channel 430. Channel 430 is fluidly connected to a horizontal channel 432. The forward most end of the channel 432 comprises a nipple 434 that is sealingly mated with a corresponding port formed in the IOL cartridge 316.

Figure 45:
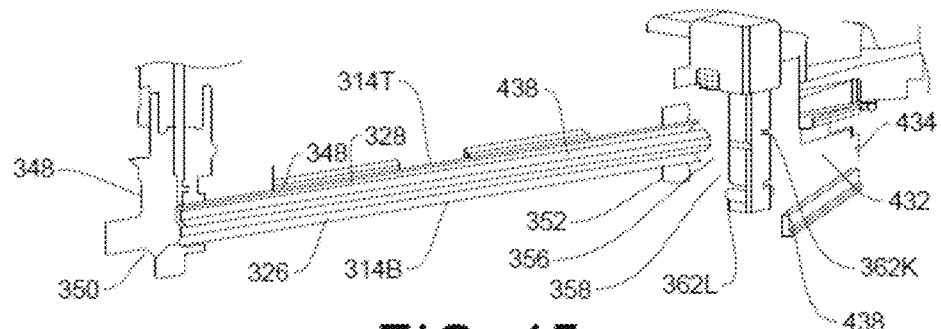
FIG. 45 is an enlarged partial cut-away view of FIG. 39 illustrating the first bleed channel inside the valve housing.

FIG. 45 illustrates the first bleed channel 356 inside the valve housing 362H that fluidly connects the end of the hydraulic tube 326 to the valve cylinder 358

Figure 46:
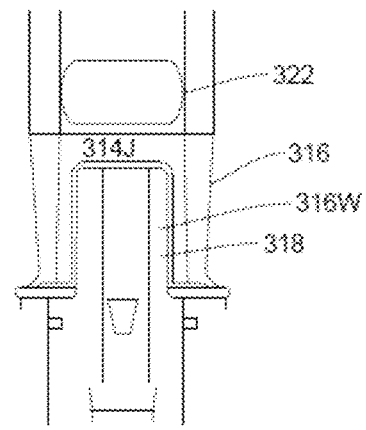
FIG. 46 is an enlarged partial cut-away view of FIG. 39 illustrating the IOL cartridge and its visualization window.
Figure 47:
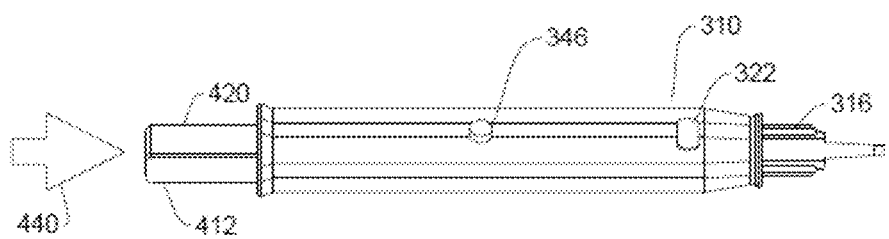
FIGS. 47-49 are enlarged partial cut-away views of FIG. 39 showing the charging the inserter by means of the charging plunger.

FIG. 46 better illustrates the IOL cartridge 316 and its visualization window 316W which allows the visualization of the IOL 318 and the OVD fluid filling the cartridge 316 to the desired, manufacturers' suggested level. Step two involves charging the IOL inserter 310.

After filling with OVD fluid in Step 1 (FIGS. 40-46), in Step 2 (FIGS. 47-49) involve charging the inserter 310 by means of the charging plunger 420 which is forcibly pushed into the rear of the outer shell housing 314 as shown by arrow 440 (FIG. 47) up to a depth indicated by a charge indication line 442. Comparing FIG. 39 with FIG. 48, it is seen that the charging plunger 420 comprises mating left and right portions 420L and 420R each having forwardly extending flat thin legs 444 that reciprocate in grooves 446 formed in the left and right sides of the outer shell housing 314. The outside surface of the legs 444 include a catch 448 that snap over corresponding protrusions 450 formed on the inner wall of the outer shell housing 314. The catches/protrusions 448/450 allow the legs 444 to be snapped into position shown in FIG. 39, allowing forward movement but precluding any backward rearward movement.

Figure 48:
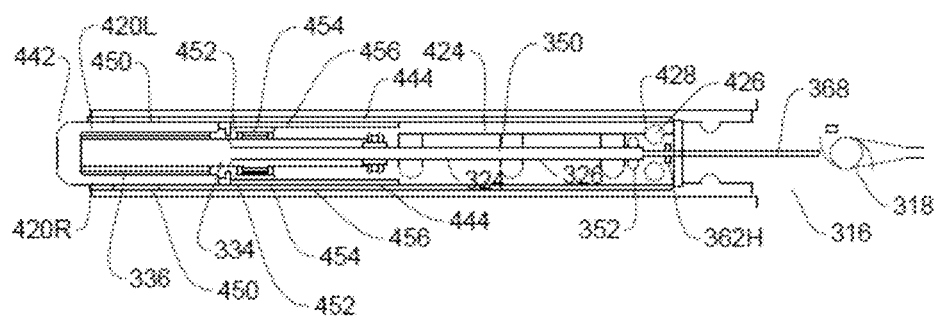
Figure 49:
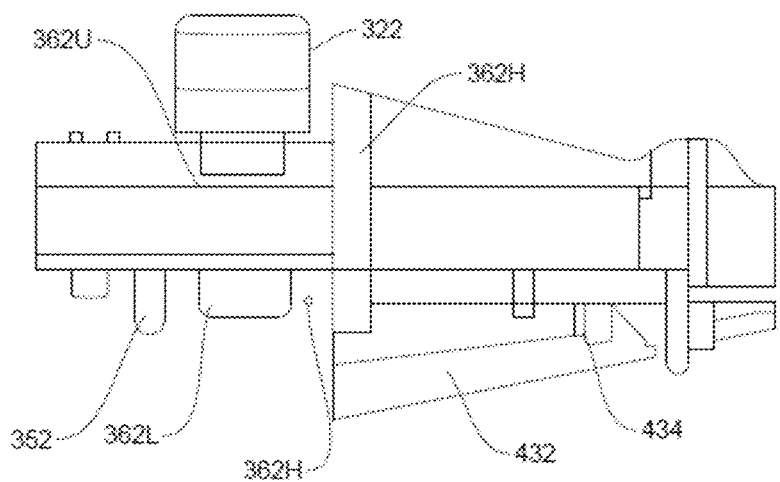

The high pressure spraying 336 is positioned over the end of a boss 382 extending rearwardly from the head 334 of the piston 324. In this position shown in FIG. 39, a pair of inwardly extending pawls 452 engage under the head 334 of the piston 324 to keep the spring 336 compressed within the charging plunger 420. However, once the charging plunger 420 is forcibly pushed (see FIG. 47) fully into the rear of the inserter 310 (FIG. 48), the pawls 452 are spread apart by tabs 454 inwardly extending from the outer shell housing 314. The pawls 452 engage and spread the pawls 452 outwardly apart as shown in FIG. 48 as the charging plunger 452 is forced inwardly, thereby releasing the head 334 of the piston 324. It is noted that the pawls 452 are allowed to expand outwardly by tabs 454 by virtue of the space between the legs 444 and the inner lumen of the outer shell housing 314. It is also noted that additional protrusions 456 are aligned with the fully-inward position of the charging plunger 420 to allow catches 448 to snap over and be retained thereby to securely hold the charging plunger 420 in its charging position shown in FIG. 48. It is also noted that when the charging plunger 420 is in its fully-inward position, the indicator line 442 is no longer visible because it is moved inside the rear of the housing 314, thereby visually indicating that the plunger 420 has been pushed the desired distance into the rear of the housing 314.

Simultaneously with forcibly pushing the plunger 420 into the rear of the housing 314, one of the legs 444 engages and slides forward the unlatching mechanism 410 which moves its cut out portion 428 in alignment with the slot 412S in the leg 412 of the button 320, thereby allowing the button 320 to pop up to its closed position. It is noted that in the closed position, the lower O-ring 362L has moved upwardly from the frustro-conical portion 430FC into the circular cylindrical valve cylinder 358 to seal therewith, thereby precluding any OVD fluid flow therethrough.

Also simultaneously with forcing the plunger 420 into the rear of the housing 314, the piston 324 is likewise forced forwardly. Upon forward movement of the piston 324, the first O ring 350 moves into the hydraulic tube 326 to form a seal with its inner lumen entrapping OVD fluid therein while at the same time precluding any leakage back through the fill port 346.

Figure 50:
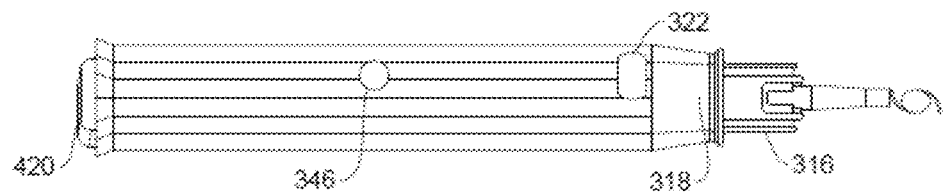
FIGS. 50-52 are enlarged partial cut-away views of FIG. 39 showing the deploying the IOL into the patient's eye.
Figure 51:
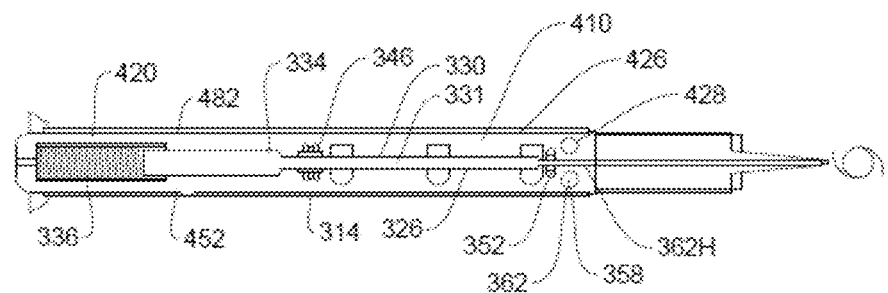
Figure 52:
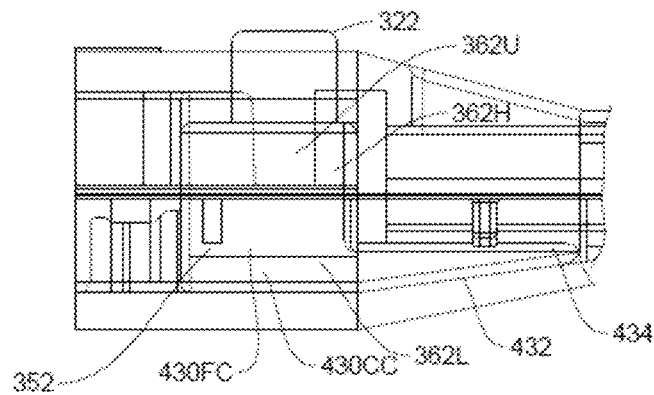
Figure 53:
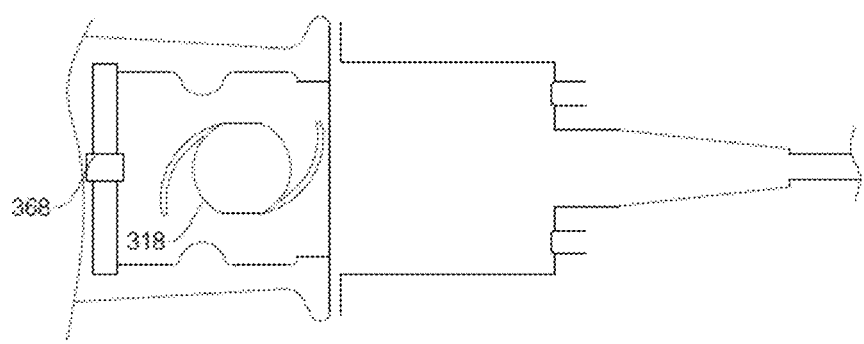
FIG. 53-54 are enlarged partial cut-away views of FIG. 39 showing the IOL adapted to be used with a variety of IOL cartridges.
Figure 54:
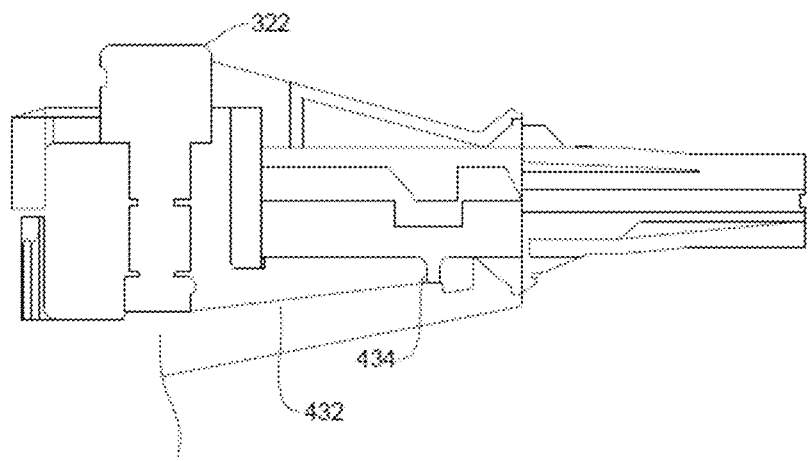

As shown in FIGS. 50-52, Step 3 comprises deploying the IOL 318 into the patient's eye. Deployment occurs by depressing upon the button 322 to open the valve 362 (see FIG. 43) allowing OVD fluid to flow from hydraulic chamber 331 inside the hydraulic tube 326 into the valve housing 362H through the first bleed channel 356 into the valve cylinder 358, around the periphery of the valve element 362 and lower O-ring 362L and the valve cylinder 358, then over the surface of the lower O ring 362L and into the channel 432. It is noted that due to the frustro-conical portion 430FC, further depressing of the button 322 increases the flow rate of the OVD fluid as the lower O ring 362L moves downwardly along the length of the frustro-conical portion 430FC, thereby allowing the surgeon to have precise control over the rate of delivery of the IOL 318 into the patient's eye.

As the OVD fluid is bled from the hydraulic chamber 331 by depressing button 322, the piston 324 is allowed to move forward under pressure from spring 336. Such forward movement of the piston 324 causes the tip 368 of the piston to fully deliver the IOL 318 into the patient's eye. It is noted that the OVD fluid being bled from the hydraulic chamber 331 flows into the IOL cartridge 316.

As noted above and illustrated in FIGS. 53 and 54, the IOL inserter 310 of the invention may be adapted to be used with a variety of IOL cartridges 316 (AMO is merely illustrative). In this regard, the manufacturer's IOL cartridge 316 will have to be adapted to fit into the forward end of the outer shell housing 314 such as including locating and retention features (i.e., notches). Further, the tip 368 of the piston 324 would be optimally designed according to the manufacturer's specifications to properly engage that manufacturer's IOL 318 for proper folding of the IOL 318 in the IOL cartridge 316 and delivery into the patient's eye.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,

What is claimed is:

1. An intraocular lens inserter, comprising in combination:
    an IOL cartridge;
    an outer shell housing having a longitudinal cylinder;
    a hydraulic housing having a longitudinal bore, said hydraulic housing being positioned in said outer shell housing;
    a hydraulic piston, said hydraulic piston including a smaller-diameter portion extending through said longitudinal bore and a larger-diameter portion extending into said longitudinal cylinder, a diameter of said smaller-diameter portion being smaller in diameter than a lumen of said longitudinal bore to define an annular hydraulic chamber, said hydraulic piston further including at one end a piston head dimensioned to slide within said longitudinal cylinder and at another end a tip to mechanically deliver the intraocular lens;
    a high pressure compression spring engaging said piston head to constantly urge said piston forwardly;
    said hydraulic housing including a fill port connected in fluid communication with said hydraulic chamber for filling said hydraulic chamber with a fluid to hydraulically resist said spring from urging said piston forwardly;
    a first bleed channel extending from said hydraulic chamber to a valve cylinder;
    a second bleed channel extending from said valve cylinder to the IOL cartridge;
    a valve element positioned within the valve cylinder to bleed said fluid from said hydraulic chamber into the IOL cartridge and thereby hydraulically control the forward movement of said tip to mechanically deliver the intraocular lens; and
    an operation button connected to said valve element for opening said valve element permitting such bleeding of fluid from said hydraulic chamber.

2. The intraocular lens inserter as set forth in claim 1, wherein said valve cylinder extends vertically and wherein the second bleed channel is at a higher level than said first bleed channel.

3. The intraocular lens inserter as set forth in claim 2, further including upper and lower O-rings positioned on said valve element and spaced apart along the length thereof such that when said O-rings straddle said bleed channels, fluid flow is established between said hydraulic chamber and the IOL cartridge and such that when said valve element is positioned such that said lower O-ring is above said first bleed channel, fluid flow from said hydraulic chamber and the IOL cartridge is blocked.

4. The intraocular lens inserter as set forth in claim 3, further including a spring entrained underneath said button and a notch in said hydraulic housing to urge said button upwardly.

5. The intraocular lens inserter as set forth in claim 4, further including a catch for keeping said button downwardly to an open position allowing fluid flow from said hydraulic chamber into the IOL cartridge to fill the IOL cartridge.

6. The intraocular lens inserter as set forth in claim 5, wherein said catch is released when the IOL cartridge is fully inserted and seated in said hydraulic housing, whereupon said spring urges said button to move upwardly to close fluid flow from said first bleed channel to said second bleed channel.

7. The intraocular lens inserter as set forth in claim 6, wherein depressing of said button against the resiliency of said spring moves said valve element downwardly to the point where said O-rings straddle said first bleed channel to bleed said fluid from said hydraulic chamber into the IOL cartridge and wherein said tip of said small-diameter portion extends further into the IOL cartridge to deliver the IOL.

8. The intraocular lens inserter as set forth in claim 3, wherein said valve cylinder comprises a circular-cylindrical portion and a frustro-conical portion.

9. The intraocular lens inserter as set forth in claim 8, wherein, when said lower O ring moves from inside said circular-cylindrical portion of said valve cylinder into said frustro-conical portion, fluid bleeds around said lower O-ring said second bleed channel.

10. The intraocular lens inserter as set forth in claim 1, further including the fill port including an elastomeric stopper capable of being pierced by a hypodermic needle of a syringe filled with the fluid so that the fluid may be injected to fill said hydraulic chamber.

11. The intraocular lens inserter as set forth in claim 10, wherein, during use, depressing said button against the resiliency of said spring moves said valve element downwardly until said O-rings straddle said first bleed channel allowing fluid to bleed from said hydraulic chamber and into the IOL cartridge by the force of said spring to force said piston forwardly in a smooth and deliberate speed to move said tip of said small-diameter portion to extend further into the IOL cartridge to deliver the IOL.

12. The intraocular lens inserter as set forth in claim 11, wherein, during use, upon releasing said button, said spring returns said valve element to its closed position.

13. The intraocular lens inserter as set forth in claim 1, further including a first O-ring positioned about said larger-diameter portion of said piston close to a transition to said smaller-diameter portion to seal against said lumen of said longitudinal bore as said piston moves forwardly, thereby forcing the fluid within said hydraulic chamber through said button.

14. The intraocular lens inserter as set forth in claim 13, wherein a front end of said longitudinal bore steps down to a reduced diameter equal to that of said small-diameter portion of said piston and a second O-ring is positioned at said step to sealingly engage around said smaller-diameter portion of said piston to prevent fluid in said hydraulic chamber from leaking therethrough.

15. The intraocular lens inserter as set forth in claim 1, further including a slider that interfaces the IOL cartridge to the inserter.

16. The intraocular lens inserter as set forth in claim 15, wherein said slider comprises a front receptacle adapted to receive the IOL cartridge, said slider comprising a pair of rearwardly-extending parallel arms having outer rails that engage into corresponding longitudinal slots formed on inside sides of said outer shell housing.

17. The intraocular lens inserter as set forth in claim 16, wherein said slider is held in a fully inward position by a resilient catch formed in a bottom of said outer shell housing such that when said slider is snapped into position by the catch, said valve element moves upwardly to its closed position, whereby when the IOL cartridge is inserted into said slider but not fully seated, said valve element is held downwardly so that the fluid may flow from said hydraulic chamber into the IOL cartridge and when the IOL cartridge is fully inserted and seated in said hydraulic housing, said valve element moves upwardly to block fluid flow from said first bleed channel to the second bleed channel.

18. The intraocular lens inserter as set forth in claim 1, wherein the inserter comprises an ergonomic design allowing for one-handed operation.

19. The intraocular lens inserter as set forth in claim 1, wherein said longitudinal bore comprises a hydraulic tube in which is positioned said smaller diameter portion of said hydraulic piston.

20. The intraocular lens inserter as set forth in claim 19, wherein leakage about a periphery of said hydraulic tube is precluded by a first O ring positioned about a forward end of said hydraulic tube and a second O-ring positioned about a rearward end of said hydraulic tube.

21. The intraocular lens inserter as set forth in claim 19, further including an O-ring positioned about said tip.

22. The intraocular lens inserter as set forth in claim 19, wherein said fill port comprises a generally circular bore having a forward portion in which a rearward end of said hydraulic tube is sealingly inserted.

23. The intraocular lens inserter as set forth in claim 1, wherein said fill port comprises a Luer fitting.

24. The intraocular lens inserter as set forth in claim 1, wherein said spring is entrained between said piston head and a rear wall of a charging plunger that compresses said spring when pushed into a rear of said outer shell housing.

25. The intraocular lens inserter as set forth in claim 24, wherein said charging plunger comprises mating left and right portions, each having forwardly extending flat thin legs that reciprocate in grooves formed in left and right sides of said outer shell housing.

26. The intraocular lens inserter as set forth in claim 25, wherein each outside surface of said legs include a catch that snap over corresponding protrusions formed on an inner wall of said outer shell housing to allow, upon charging, forward movement but precluding any rearward movement.

27. The intraocular lens inserter as set forth in claim 26, wherein said piston head comprises a boss over which is positioned said spring and wherein charging plunger comprises a pair of inwardly extending pawls that engage under said piston head to entrain said spring within said charging plunger.

28. The intraocular lens inserter as set forth in claim 27, further including tabs inwardly extending from said outer shell housing to spread said pawls apart when said charging plunger is pushed into said outer shell housing, thereby releasing said piston head.

29. The intraocular lens inserter as set forth in claim 28, wherein said charging plunger further includes said catches to snap over and be retained by protrusions to hold said charging plunger in its charging position.

30. The intraocular lens inserter as set forth in claim 27, further including an indicator line to visually indicate whether said charging plunger has been charged by being pushed into said rear of said outer shell housing.

31. The intraocular lens inserter as set forth in claim 25, further including an unlatching mechanism that allows said valve element to move to its closed position when said charging plunger is pushed into said rear of said outer shell housing.

\* \* \* \* \*